US007065983B2

(12) United States Patent
Trinh et al.

(10) Patent No.: US 7,065,983 B2
(45) Date of Patent: Jun. 27, 2006

(54) ADHESIVE ICE BAG DEVICE

(76) Inventors: Albert Long Trinh, 8671 Creekwood La., Maineville, OH (US) 45039; David Lam Trinh, 8671 Creekwood La., Maineville, OH (US) 45039

( * ) Notice: Subject to any disclaimer, the term of this patent is extended or adjusted under 35 U.S.C. 154(b) by 102 days.

(21) Appl. No.: 10/455,886

(22) Filed: Jun. 6, 2003

(65) Prior Publication Data

US 2004/0244413 A1 Dec. 9, 2004

(51) Int. Cl.
*F25D 3/08* (2006.01)

(52) U.S. Cl. ............................. 62/530; 62/259.3; 607/96; 607/112

(58) Field of Classification Search .................. 62/530, 62/259.3, 457.2, 371; 607/96, 112, 114
See application file for complete search history.

(56) References Cited

U.S. PATENT DOCUMENTS

| | | | |
|---|---|---|---|
| 2,403,676 A | | 7/1946 | Modlinski |
| 2,563,933 A | * | 8/1951 | Hipps et al. .................. 383/86 |
| 2,595,328 A | * | 5/1952 | Bowen ........................ 607/114 |
| 2,882,692 A | | 4/1959 | Robbins |
| 2,898,744 A | | 8/1959 | Robbins |
| 2,925,719 A | | 2/1960 | Robbins et al. |
| 3,058,313 A | | 10/1962 | Robbins |
| 3,258,065 A | * | 6/1966 | Ward ............................ 165/46 |
| 3,338,284 A | | 8/1967 | Ausnit |
| 3,476,102 A | * | 11/1969 | Sarnofrf ...................... 126/204 |
| 3,643,665 A | | 2/1972 | Caillouette |
| 3,780,537 A | | 12/1973 | Spencer |
| 3,804,077 A | * | 4/1974 | Williams .................. 126/263.1 |
| 3,885,403 A | | 5/1975 | Spencer |
| 3,893,834 A | | 7/1975 | Armstrong |
| 3,950,789 A | | 4/1976 | Konz et al. |
| 4,033,354 A | | 7/1977 | De Rosa |
| 4,263,079 A | | 4/1981 | Sutrina et al. |
| 4,363,345 A | | 12/1982 | Scheibner |
| 4,530,220 A | * | 7/1985 | Nambu et al. ................ 62/530 |
| 4,829,641 A | | 5/1989 | Williams |
| 4,846,176 A | * | 7/1989 | Golden ....................... 607/104 |
| 4,891,501 A | | 1/1990 | Lipton |
| 4,907,321 A | | 3/1990 | Williams |
| 4,910,978 A | * | 3/1990 | Gordon et al. ................ 62/530 |
| 4,986,076 A | | 1/1991 | Kirk et al. |
| 5,009,828 A | | 4/1991 | McCree |
| 5,031,418 A | * | 7/1991 | Hirayama et al. ............. 62/530 |
| 5,088,487 A | * | 2/1992 | Turner ........................ 607/108 |
| 5,800,491 A | * | 9/1998 | Kolen et al. ................. 607/108 |

* cited by examiner

Primary Examiner—Melvin Jones

(57) ABSTRACT

Ice bag covers, methods, and articles of manufacture useful in the creation of a adhesive, non-constrictive ice bag device that is compact and can be attached to a garment, said ice bag device preferably comprising (a) a flexible outer cover for one or more cooling packs, having one face partially or entirely covered with mounting adhesive for temporarily attaching said cover, when it is filled with at least one cooling pack, to the inside or the outside of a garment, such that said cooling pack is in close contact with an injured body part of the user, without the need for a strapping and/or wrapping means, and (b) optionally, but preferably, one or more liquid impermeable inner containers that are filled with a cooling medium to form said cooling packs and can fit inside said outer cover, each said inner container being preferably a plastic zipper bag which is sealed on three sides and which has the fourth side open having a rib and groove sealing closure, and wherein said article comprising said outer cover is optionally packaged in association with a set of instructions for use to direct the user how to use the product properly, to ensure that the user knows what benefits can be achieved, and how best to obtain these benefits, and a method of doing business in which an established entity, especially a sports organization is used to assure the user that the device and method of use are safe and effective.

20 Claims, 10 Drawing Sheets

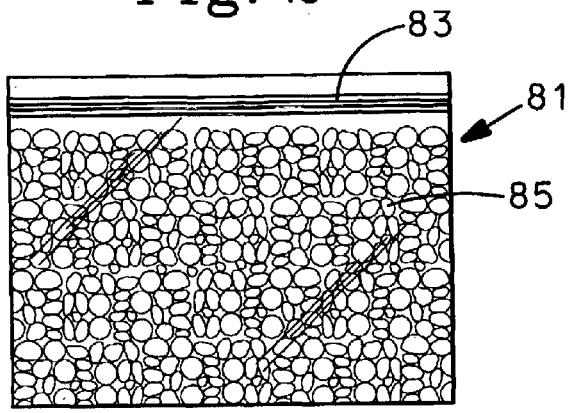
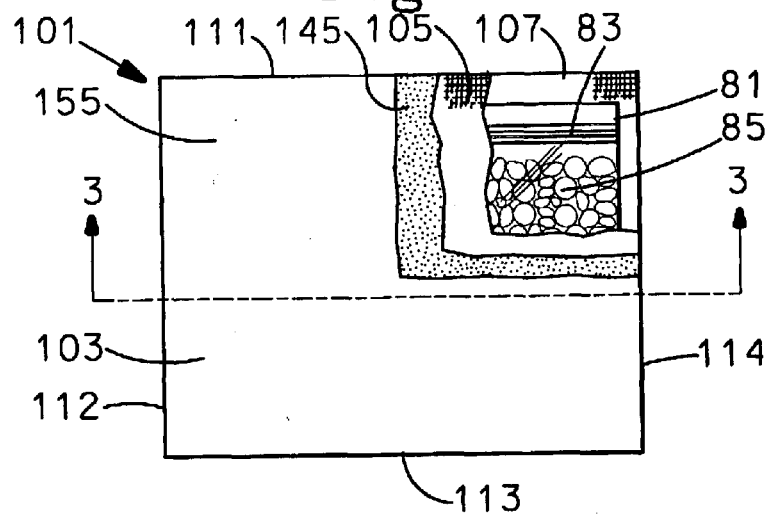
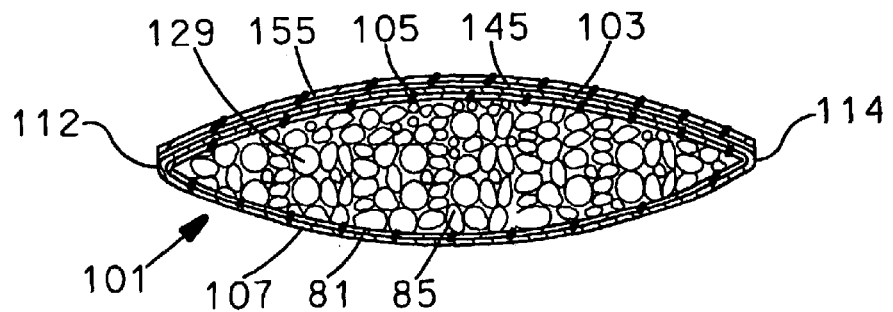

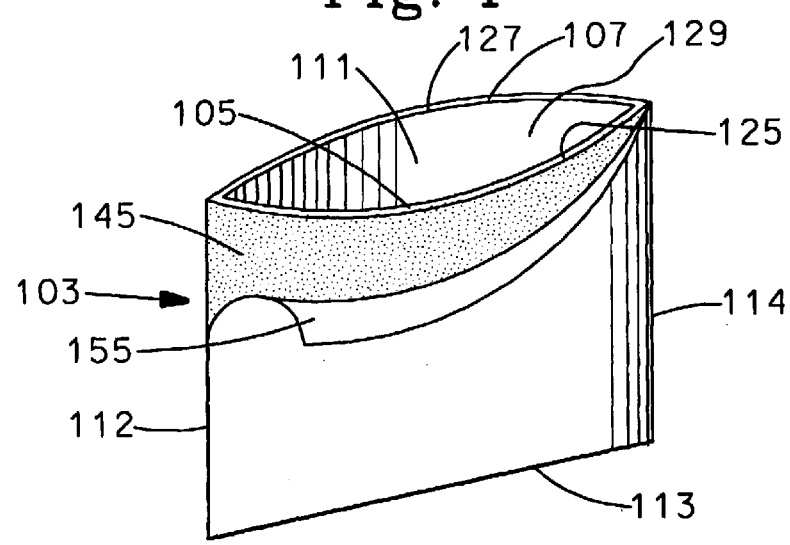
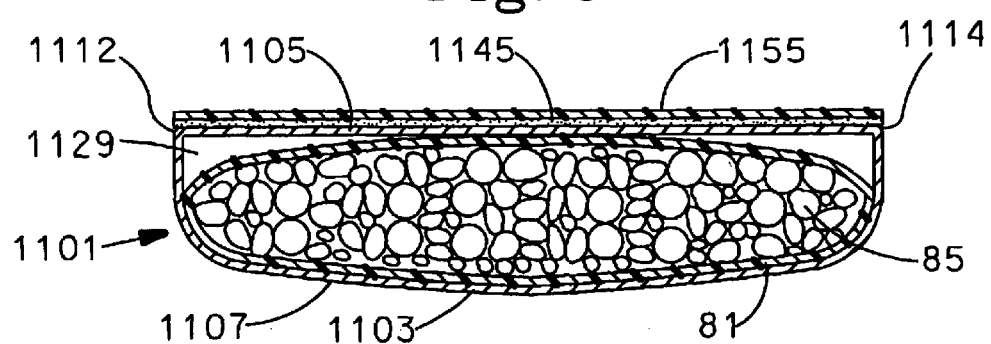

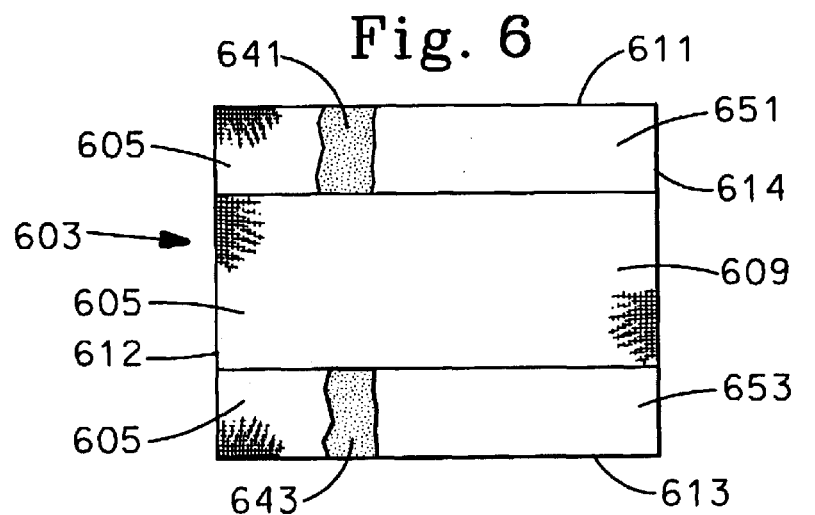
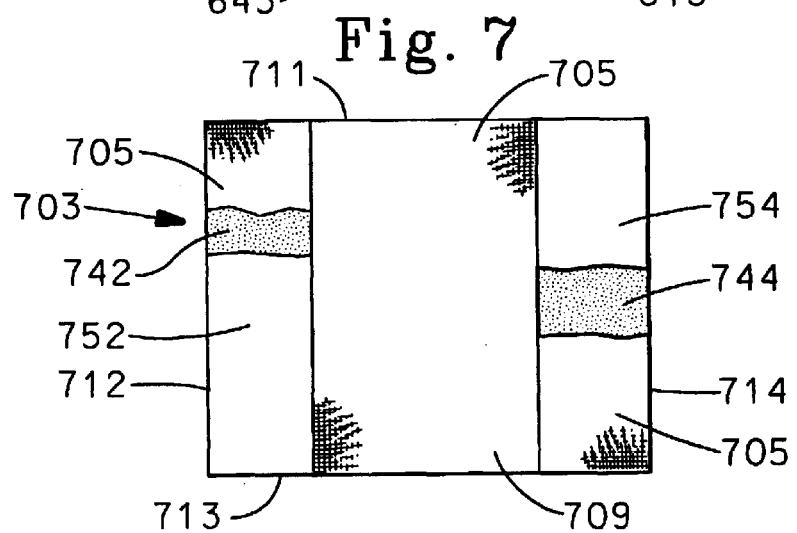
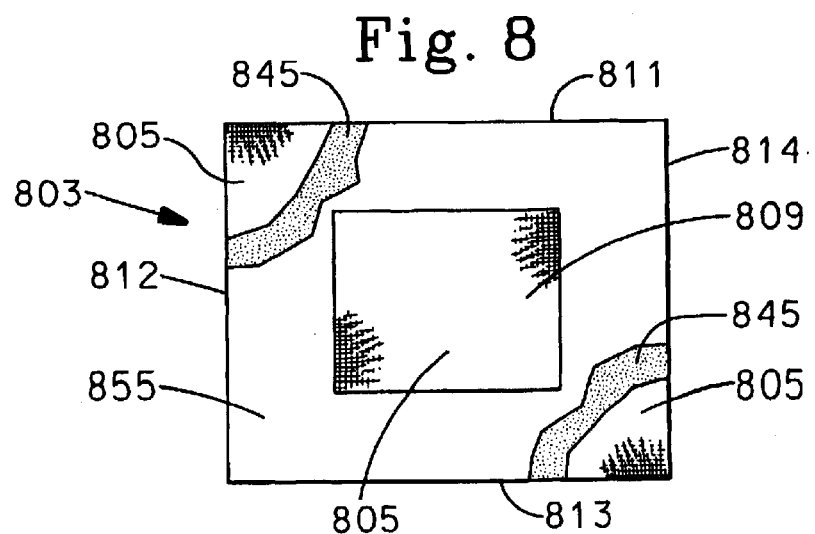

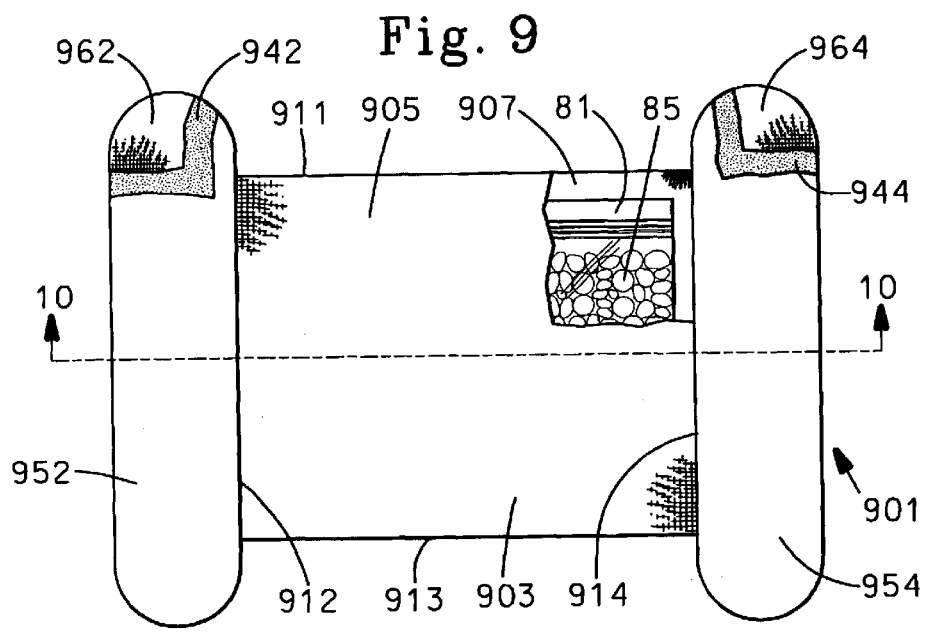
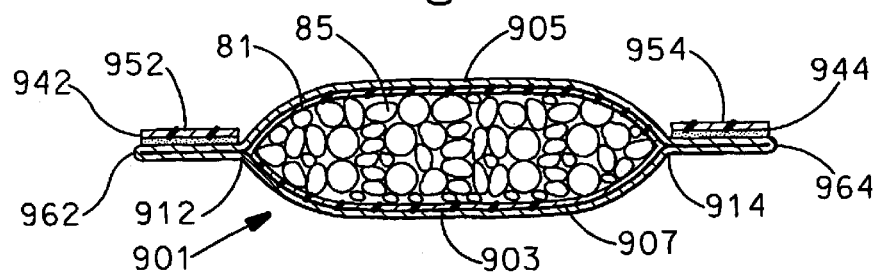
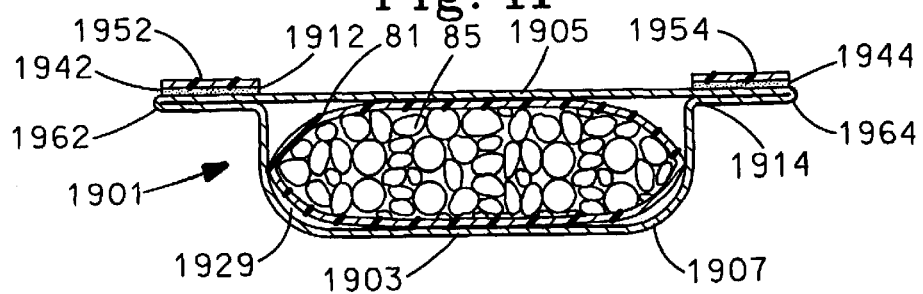

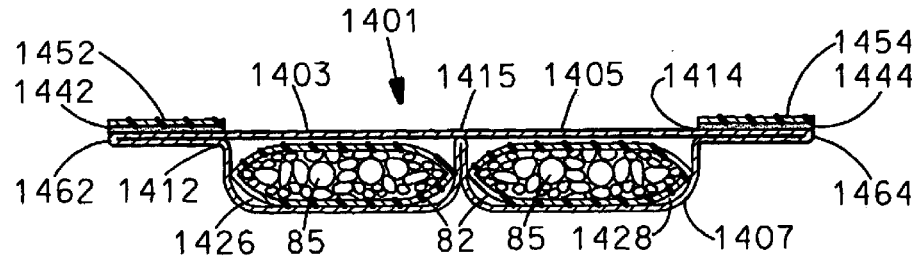
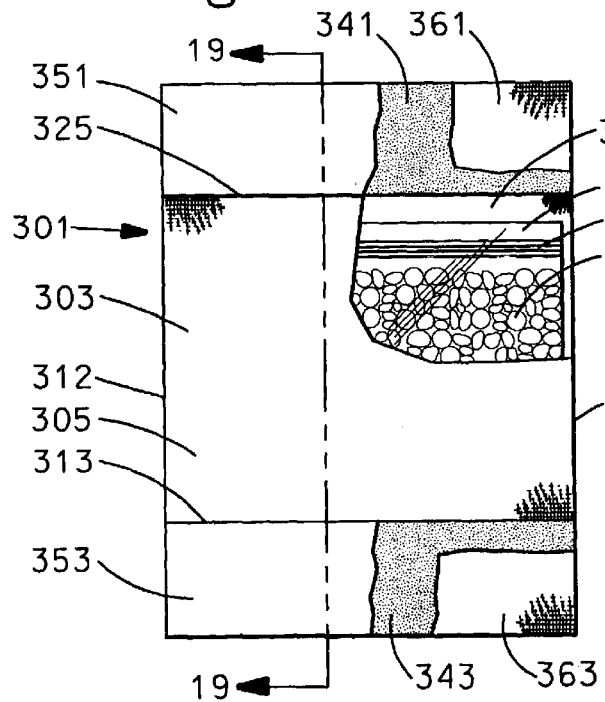
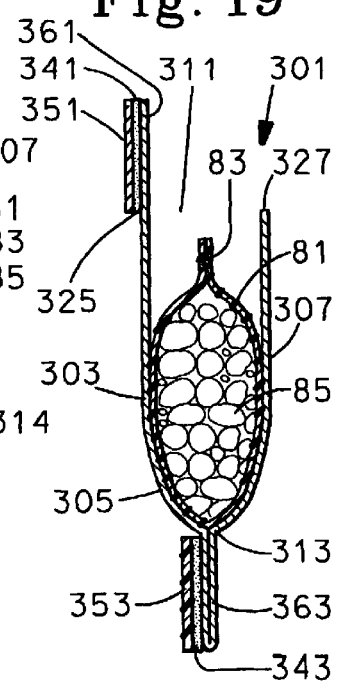

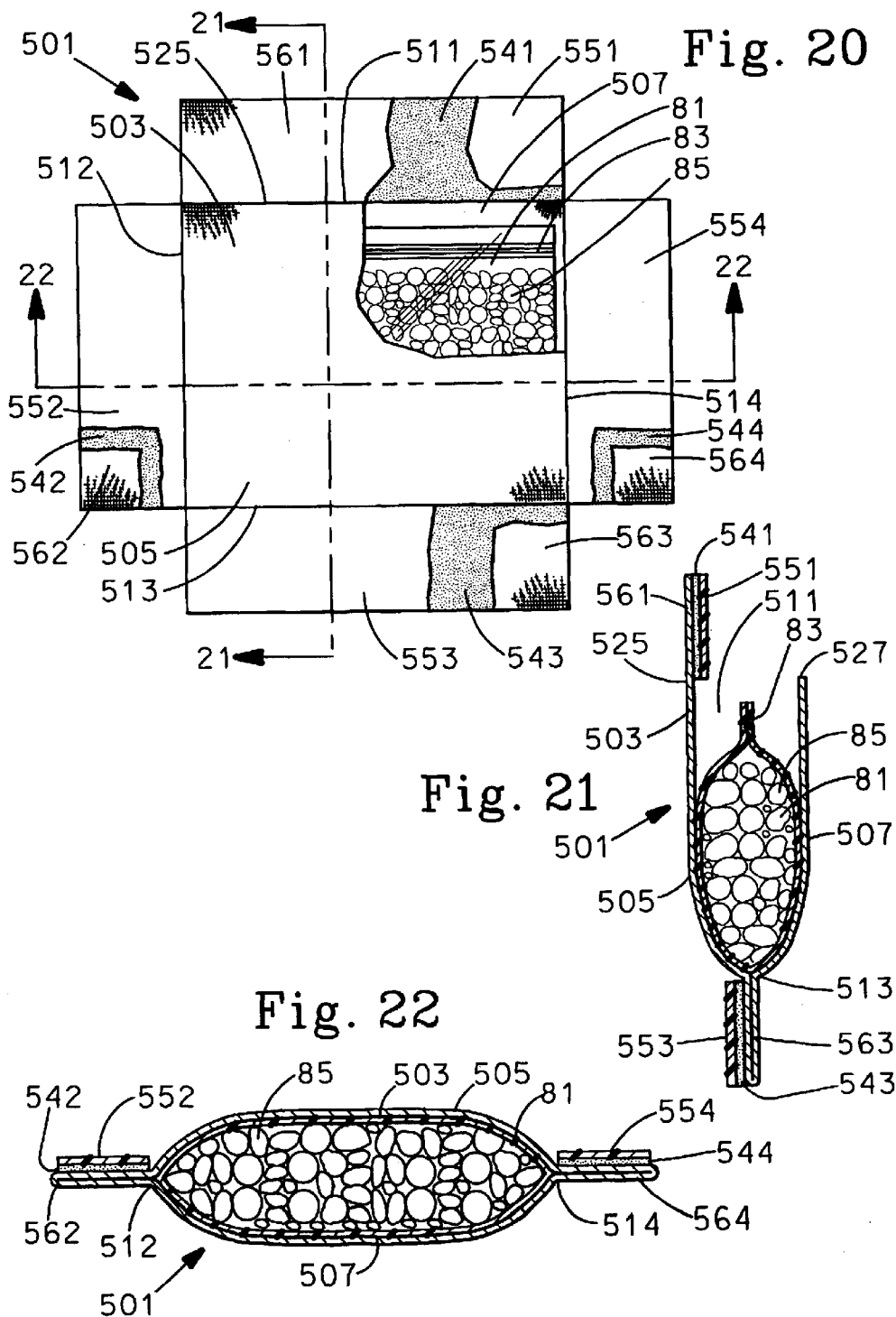

ADHESIVE ICE BAG DEVICE

BACKGROUND OF THE INVENTION

1. Field of the Invention

This invention relates to the general field of medical devices and/or methods for cooling injured body parts to, e.g., alleviate pain and inflammation. In particular, it relates to a flexible cover for "ice bags" that has an adhesive area and which can be applied to an injured body part, either directly or indirectly, with improved comfort, convenience, and/or availability by means of said adhesive area. Thus, it relates to an ice bag cover for ice bags that has an adhesive means so that it can be attached to a garment, said ice bag cover being compact, e.g., to fit in first-aid boxes to be used at home or away from home, e.g., in sporting events, such as at a soccer field or a basketball court, outings in a park, picnics, and/or on trips. It also relates to an article of manufacture that provides such cover; to the method of fabricating and/or using such ice bag device using such cover; to the provision with the cover of instructions for use that aid unskilled users to provide effective emergency assistance ("first aid treatment") to injured body parts; and to methods of doing business that promote the availability of such covers, articles of manufacture, and methods, etc., to the maximum number of people who may need such first aid treatment.

2. Description of the Related Art

The desirability of using ice bags for thermal therapy is well accepted. Ice bags enable the user to apply cold to an injury such as a bruise or sprain without unacceptable mess. A common ice bag that is commercially available is the reusable type comprising a water-impermeable, commonly a rubber-lined, flexible bag having a tubular rigid neck and a removable cap. To use, the bag is filled with ice cubes or ice chips and closed with the cap, then the bag is applied to the bruised body part and held in place by hand.

Another type of cold pack that is commercially available is a refrigeratable gel cold pack which comprises a refrigerant or coolant gel material contained in a plastic housing which can be either flexible or relatively inflexible. The gel packs are stored in a conventional freezer for chilling or cooling and are then ready for use. Also commercially available is an endothermic chemical pack that comprises two or more pouches for separately storing chemical reactants that can be mixed to produce a cooling mixture.

A common home-use ice bag can be made using a commercially available reclosable plastic sandwich and/or freezer bag with a zipper seal, such as a Ziploc™ plastic bag filled with ice (Ziploc is a registered trademark of Dow Chemical Company, Midland, Mich.). By "reclosable" it is meant that the bag can be opened and closed numerous times.

One of the disadvantages of these ice bags is that they need to be inconveniently held by hand to maintain contact with the injured body part. To overcome this inconvenience, several types of ice bag devices comprising a holder for these ice bags have been created. These ice bag devices can be strapped around a body part, with, e.g., loop and hook mating Velcro™-type fastening straps. Since ice bag devices need to be wrapped and tied around a body part, they are constrictive and can interfere with the blood flow. Furthermore, these ice bag devices are usually of complicated design, large and bulky in size and/or expensive to produce.

U.S. Pat. No. 5,887,437 issued Mar. 30, 1999 to Maxim discloses a cold pack containing sealed water or a chemical cooling mixture that does not have fastening straps, but instead has an extended perimeter with adhesive means to attach the chemical cold pack to a skin surface. However when this self-adhesive chemical cold pack is applied to an unwashed and likely profusely sweaty skin surface of a bruised body part of an athlete who is injured in the field, the sweaty and/or soiled skin surface can make a common adhesive means less adhering. The adhering means can be made to be more strongly sticky, but in this case the removal of the device from the skin surface after use can be more uncomfortable, especially when the skin area is already bruised.

To overcome the constriction effect of the strapping, there are efforts to develop garments or other devices that can provide the cold therapy without the need to be tightly strapped and/or wrapped. U.S. Pat. No. 2,403,676 issued Jul. 9, 1946 to Modlinski discloses a jacket with a plurality of attached pockets to hold ice packs or ice bags. U.S. Pat. No. 4,891,501 issued Jan. 2, 1990 to Lipton discloses a therapeutic pad, with cooling elements, that can be hung around the neck or the head to treat the muscles of the neck, the chest, the back, and/or the jaw. U.S. Pat. No. 5,167,655 issued Dec. 1, 1992 to McCoy discloses a cold therapy panty provided with a receptacle located adjacent to the crotch area to receive a cold pack for applying cold therapy to the crotch of the wearer. U.S. Pat. No. 4,033,354 issued Jul. 5, 1977 to De Rosa discloses an ice cooling vest-like garment comprising water-filled pockets that are frozen and subsequently attached via Velcro fasteners to the inside of the garment so as to provide body cooling under heat stress conditions. Although these cold pack devices provide an improvement over the prior art, they are of complicated design, large and bulky in size and/or expensive to produce.

Thus, there is a need for an improved, inexpensive and readily available ice bag device that has a means for attaching it to a user's clothing such that said ice bag device is in close contact with an injured body part of the user, and eliminates the necessity for holding it by hand or strapping and/or tying it around a body part. Preferably such ice bag device is compact, not bulky, so that preferably it can fit in a first-aid box along with other first-aid items. Preferably such ice bag device is easily manufactured and used.

SUMMARY OF THE INVENTION

This invention relates to a flexible outer cover for a cooling medium, having a layer of mounting adhesive to temporarily attach said cover, when it is filled with the cooling medium or one or more cooling packs containing the cooling medium, to the inside or the outside of a garment, such that said cooling medium is in close contact with an injured body part of a user, without the need for a strapping and/or wrapping means. In a preferred embodiment, the outer cover is self-adhering with the adhesive layer being an integral part of the outer cover and entirely or partially covering one side of the outer cover. In another preferred embodiment, the outer cover is not self-adhering, but with the adhesive layer being separated from the outer cover and being in the form of one or more adhesive strips, such as bandage adhesive strips or adhesive bandage strips, that are used to attach the outer cover to the garment. The adhesive layer is preferably hypoallergenic. The adhesive layer is optionally and preferably covered with a release paper layer to protect the adhesive from prematurely sticking to a surface other than the intended user's garment. In one preferred aspect, the outer cover has one open end to receive one or more inner cooling bags or packs, hereinafter simply "pack" or "packs", containing a cooling medium. Each inner cooling pack comprises either a resealable or permanently sealed fluid impermeable plastic container containing a cooling medium, preferably either ice, water, ice and water combination, refrigeratable cooling gel, or endothermic chemical cooling mixture. In another aspect, the outer cover is closed and contains one or more inner cooling packs, wherein each cooling pack comprises a permanently sealed fluid impermeable plastic container containing a cooling medium.

This invention also relates to a method for first aid treatment of injuries by attaching the outer cover hereinabove which holds one or more inner fluid impermeable plastic containers containing a cooling medium to a garment so as to apply said cooling medium to an injured body part when the garment is worn. In a preferred embodiment it relates to a method of creating a non-constrictive ice bag device using said outer cover by filling one or more plastic zipper containers sealable by interlocking rib and groove sealing closure, with ice or an ice and water combination, placing the filled container(s) inside said outer cover, using the adhesive layer to attach the assembled ice bag device to the inside or the outside of a garment, such that said ice bag device is in close contact with an injured body part of the user when the garment is worn. The present invention also relates to the fully assembled non-constrictive ice bag device prepared by the said method, said ice bag device comprising an outer cover and at least one inner cooling pack. In an alternative embodiment of this method, the inner cooling pack comprising a resealable zipper container containing ice can be replaced by an endothermic chemical system pack or a permanently sealed cooling pack containing ice or cooling gel, when such cooling pack is available.

The present invention also relates to the association of instructions for use with the non-constrictive ice bag device disclosed hereinabove, or with the method using said device, to ensure that the method can be practiced efficiently, quickly, and effectively so as to maximize the effect of the cooling treatment on an injury.

The present invention also relates to an article of manufacture comprising the flexible outer cover hereinabove, optionally, one or more resealable or permanently sealed liquid impermeable containers disclosed hereinabove, optionally, a sealed plastic wrapper to keep the outer cover and the optional elements in a hygienic, non-contaminated condition in storage, and optionally packaged in association with instructions for use comprising an instruction to direct the consumer to attach the assembled ice bag device to the inside or the outside of a garment.

The present invention also relates to a method of doing business in which the outer cover, the ice bag device, the article of manufacture, and/or the instructions for following the method disclosed hereinabove and/or the article, are distributed with the approval of one or more organizations so as to maximize the availability of the cover, the ice bag device and/or method where they are needed and/or to provide assurance that the method, device, instructions, etc. are effective and safe.

The present invention also relates to a method of using an adhesive means to attach an ice bag device to a garment such that said ice bag device is in close contact with an injured body part of a user when the garment is worn, wherein said ice bag device comprises a flexible outer cover containing an inner container filled with a cooling medium.

BRIEF DESCRIPTION OF THE DRAWINGS

FIG. 1 is a plan view of a self-adhering ice bag device of the present invention, comprising an outer cover with a sack structure having one open end, and containing an inner resealable plastic zipper container containing ice chips, said outer cover being partly cut away to show said ice-filled zipper container;

FIG. 2 is a plan view of the isolated zipper container filled with ice chips of the ice bag device of FIG. 1;

FIG. 3 is a cross-sectional view of the ice bag device of FIG. 1 taken along the line 3—3;

FIG. 4 is a perspective oblique view of the outer cover of the ice bag device of FIG. 1;

FIG. 5 is a cross-sectional view of a preferred version of the ice bag device of FIG. 1 taken along the line 3—3;

FIG. 6 is a plan view of an alternative embodiment of the self-adhering outer cover of the present invention, with a sack structure having one open end and two adhesive strips, wherein one adhesive strip is located close to the open end of the outer cover and the other strip located at the opposite edge;

FIG. 7 is a plan view of an alternative embodiment of the self-adhering outer cover of the present invention, with a sack structure having one open end and two adhesive strips, wherein the two adhesive strips are located at the opposite closed edges of the outer cover;

FIG. 8 is a plan view of an alternative embodiment of the self-adhering outer cover of the present invention, with a sack structure having one open end and a four-sided adhesive strip that borders all the four edges of the outer cover;

FIG. 9 is a plan view of an alternative embodiment of the self-adhering ice bag device of the present invention, comprising an outer cover with a sack structure having one open end and two extended peripheries covered with mounting adhesive and containing a resealable plastic zipper container containing ice chips, said outer cover being partly cut away to show said ice-filled zipper container;

FIG. 10 is a cross-sectional view of one variation of the ice bag device of FIG. 9 taken along the line 10—10;

FIG. 11 is a cross-sectional view of another preferred version of the ice bag device of FIG. 9 taken along the line 10—10;

FIG. 17 is a cross-sectional view of another preferred version of the ice bag device of FIG. 14 taken along the line 16—16;

FIG. 18 is a plan view of an alternative embodiment of the self-adhering ice bag device of the present invention, comprising an outer cover with a sack structure having one open end and two extended peripheries covered with mounting adhesive and containing a resealable plastic zipper container containing ice chips, said outer cover being partly cut away to show said ice-filled zipper container;

FIG. 19 is a cross-sectional view of the ice bag device of FIG. 18 taken along the line 19—19;

FIG. 20 is a plan view of an alternative embodiment of the self-adhering ice bag device of the present invention, comprising an outer cover with a sack structure having one open end and four extended peripheries, wherein the periphery that is extended from the open end has an adhesive layer on the reverse side, for use as a closure means to tightly contain the inner cooling pack, said outer cover being partly cut away to show said cooling pack, which is an ice-filled zipper container;

FIG. 21 is a cross-sectional view of the ice bag device of FIG. 20 taken along the line 21—21;

FIG. 22 is a cross-sectional view of the ice bag device of FIG. 20 taken along the line 22—22;

As shown in FIG. 26, when the adhesive layer is a separate element from the outer cover, it can be provided by an adhesive tape. The adhesive tape can be a sport tape or a bandage adhesive tape used for making bandages. A part (a segment) 91 of one or more strips 90 of the adhesive tape is attached to the outer cover 2603 of the ice bag device 2601, and another part 92 to the clothing.

DETAILED DESCRIPTION OF THE INVENTION

Figure 12:
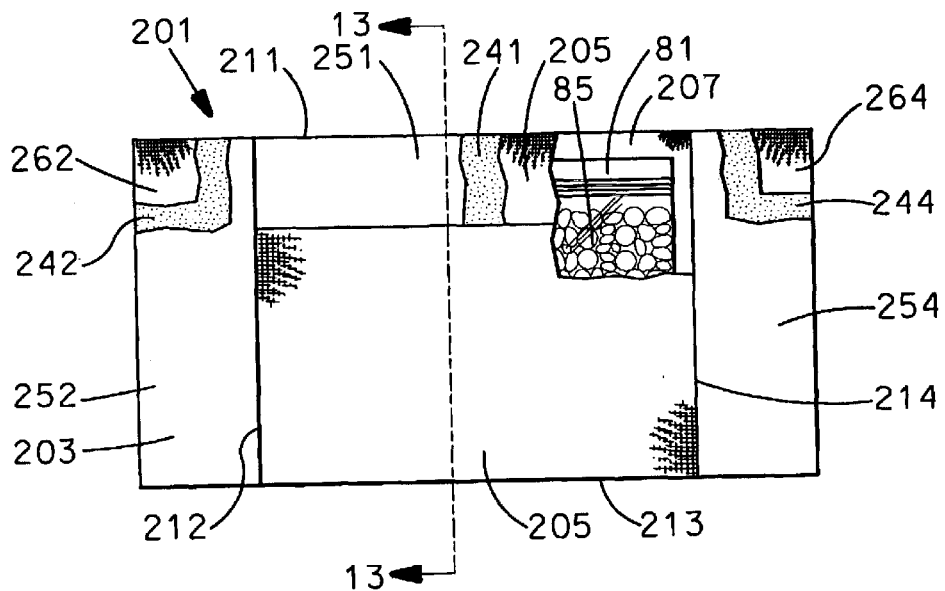
FIG. 12 is a plan view of an alternative embodiment of the self-adhering ice bag device of the present invention, comprising an outer cover with a sack structure having one open end, one adhesive strip located close to the open end, and two extended peripheries covered with mounting adhesive, and containing a resealable plastic zipper container containing ice chips, said outer cover being partly cut away to show said ice-filled zipper container.

Youth contact sport activities such as soccer, football and basketball are more and more popular. Unavoidably, these activities are accompanied by some occasional injuries such as sprains or bruises. Thus, there is a need for an inexpensive and readily available ice bag device for such events. Such ice bag devices need to be attachable in some manner without being held by hand, because while the injured player would likely prefer to stay to watch until the end of the game, he or she does not want to hold the ice bag with his or her hand for the duration of the game. Applying the ice bag device by hand not only is inconvenient, but it also can restrict the mobility if the injury is, e.g., in a lower part of the body such as in the leg or foot, and it can be awkward if the injury is, e.g., in a hard to reach body part such as on the back. Also, the hand can become uncomfortably cold. Furthermore, such ice bag device preferably should not be strapped and/or tied around a body part, because such strapping can be constrictive and can interfere with the blood flow. It is also preferred that the cold should not reduce the skin temperature excessively since that can cause damage, e.g., frostbite. Injuries that need an ice bag treatment also can happen during other types of outdoor activity such as picnicking, hiking and on other outings, and/or on trips. Such ice bag device needs to be compact, not bulky, so that preferably it can fit in a first-aid box along with other first-aid items. Preferably such ice bag device is easily manufactured and used.

In one aspect of this invention there is provided a flexible outer cover for a non-constrictive adhesive ice bag device, having a layer of mounting adhesive for use to temporarily attach said outer cover to the inside or the outside of a garment, at a location on the garment that is in close contact with the injured area of the body, when the garment is worn, without the need for a strapping and/or wrapping means, and wherein said cover has a sack structure (or pouch structure) having appropriate dimensions to form one or more compartments suitable for containing one or more inner cooling packs containing a cooling medium.

"Garment", as used herein, means a piece of clothing that is worn to cover a part of the body, such as shirt, jacket, coat, pants, trousers, shorts, underwear, hat, headband, sock, scarf, glove, and the like.

The flexible outer cover is preferably a unitary structure, typically either a sack structure (or pouch structure) with one open end to receive one or more inner cooling packs, wherein each cooling pack comprises either a resealable or a sealed fluid impermeable, preferably plastic, container containing a cooling medium, or a closed sack structure containing one or more inner cooling packs, wherein each cooling pack comprises a said permanently sealed fluid impermeable plastic container containing a cooling medium. The outer cover can have any suitable shape such as rectangular, square, round, oval, and the like. Preferably the flexible outer cover has a generally rectangular or square configuration when flattened to facilitate storage and to more efficiently contain typical inner cooling containers.

In a preferred embodiment, the outer cover is provided with an adhesive layer which is an integral part of the outer cover and entirely or partially covers one side of the outer cover to form a self-adhering outer cover.

In another preferred embodiment, the outer cover is not self-adhering, with the adhesive layer being separated from the outer cover and being in the form of one or more adhesive strips that are used to attach the outer cover to the garment. Non-limiting examples of adhesive strips that are useful in the ice bag device of the present invention include bandage adhesive tape that is commonly provided in a roll, adhesive bandage strips such as Band-Aid™ strips, adhesive tape such as Scotch™ tape, mailing tape, packaging adhesive tape, duct tape, masking tape, or the like, preferably bandage adhesive tape and/or adhesive bandage strips that are commonly available in first-aid kits.

When the mounting adhesive layer is an integral part of the outer cover, it is preferably covered with a peel-away release, e.g., paper or plastic, layer to protect it from prematurely sticking to a surface other than the intended user's garment. The release paper layer is preferably made of plastic film or other materials such as paper that can be coated with wax or other compositions for improved release. The release layer can extend beyond the outer edge of the adhesive layer to facilitate the removal of the release layer from the adhesive. The adhesive that is useful in the present invention is typically an adhesive used in adhesive tapes, such as bandage adhesive tapes, sport tapes, Scotch™ tapes, mailing tapes, packaging adhesive tapes, duct tapes, masking tapes, or the like, preferably bandage adhesive tapes and sport tapes. The adhesive is preferably hypoallergenic. Preferably the mounting adhesive has a stronger bond to the outer cover surface than the release layer and the garment surface so that after use, when the ice bag device is removed from the garment, the adhesive layer stays with the cover, and is not transferred to the garment. However, the bond with the garment surface should be strong enough to attach the ice bag device well to the garment surface.

The mounting adhesive layer can either cover one entire face of the outer cover as is depicted in FIG. 1, or cover only part of that face, preferably as adhesive strips that cover one or more edges of the outer cover, more preferably two adhesive strips that cover two opposite edges, as are depicted in FIG. 6 and FIG. 7, or one or more adhesive strips that cover all four edges of the outer cover, as are depicted in FIG. 8. The adhesive strips preferably have a suitable width to keep the ice bag device securely attached to the garment. Typically the adhesive strips have a width of at least about 0.5 cm, preferably at least about 1 cm, and more preferably at least about 1.5 cm.

In a preferred embodiment, the outer cover has from 1 to 4 extended peripheries (or extended edges) that are extensions from the edges of the outer cover, and are covered with a mounting adhesive layer for use to attach the outer cover to the garment, in addition to or instead of the adhesive layer on the body of the outer cover, as are depicted in FIG. 9, FIG. 12, FIG. 14, and FIG. 18. Each extended periphery along each edge can have a length that is shorter, but more preferably equal or longer than the corresponding edge. The periphery extension typically has a width of at least about 1 cm, preferably at least about 1.5 cm, more preferably at least about 2 cm, and less than about 20 cm, preferably less than about 8 cm, and more preferably less than about 6 cm.

Optionally, the outer cover can have a periphery extended from the edge of the open end, with this periphery having an adhesive strip covered the reverse side of the periphery, with respect to the mounting adhesive layer side, for use as a closure means to tightly contain the inner cooling pack in the compartment of the outer cover, as is depicted in FIG. 20. This adhesive closure means can optionally be replaced by loop and hook mating Velcro-type fastener strips.

In an alternative embodiment, the outer cover can be reused by renewing the original adhesive layer after use. This can be achieved by removing the tape and replacing it and/or by using double-sided adhesive strips that are applied over the original adhesive layers or where the original adhesive layers were placed after they are removed. It is preferred that the adhesive of the double-sided adhesive strips adhere more strongly to the outer cover than to garments or skin to facilitate removal. Replacing the tape can improve adherence to the cover when some of the adhesive remains on the cover after the double-sided tape is removed from the cover after use.

When the adhesive layer is a separate element from the outer cover, it can be provided by, e.g., a sport tape, or a bandage adhesive tape used for making bandages, by attaching part (a segment) of one or more strips of tape to the outer cover and another part to the clothing. Such bandage adhesive tape is available typically in the form of a roll that can commonly be found as an item in any first-aid kit. In some instances, where such bandage adhesive tape is not available, adhesive bandage strips such as Band Aid™ adhesive bandages can be used with one end attached to the cover and the other end attached to the garment. Using bandage tape allows one to carry only a cover that does not have an adhesive layer on its face and the bandage tape and a plastic zipper bag, such as Ziploc® bag, and yet put together an effective ice bag device in an emergency. Other types of adhesive tape, such as sport tape, Scotch™ tape, mailing tape, packaging adhesive tape, duct tape, masking tape, or the like, can also be used if they are available. In another embodiment, the present invention relates to the option of using double-sided adhesive tape to attach an ice bag device to the garment by attaching one side of the double-sided adhesive tape strips to the outer cover, and using the other side of the double-sided adhesive tape to attach the ice bag device to a garment.

The outer cover is made at least partly of a relatively flexible substrate. The substrate is typically a fabric, normally woven and/or non-woven and/or knitted, but can also be a resilient foam sheet. The outer cover can be made of material such as, but not limited to, woven, knitted, crocheted, or non-woven fabric of natural and/or synthetic fibers such as cotton, polyester, nylon, acrylic, rayon, and the like, felt, velvet, flocked material, heat-bonded plastic fiber material, such as, melt-blown, spun-bonded polyethylene or polypropylene, carded thermo-bonded polypropylene and rayon blend, solvent-laid thermally bonded polypropylene (e.g., Tyvek™ by Dupont), resilient open-cell or close-cell plastic foam sheet, porous and nonporous plastic film and/or rubber, paper, laminated materials such as laminate of rubber and non-woven layers, and the like. It is also permissible to have the outer cover be water impermeable and sealable to eliminate the need for the inner cooling pack. However, the different requirements for the outer cover and the inner pack make it highly preferable to provide both the outer cover and the inner pack. It is easier to wash the outer cover when it is fabric and it is easier to fabricate when there is no need to have it water impermeable.

The edges of the outer cover can be sealed by sewing, gluing, heat sealing, or the like, or can be integral, e.g., when formed from tubular material that requires no sealing on the side edges. The preferred material makes the outer cover of the ice bag device flexible, conformable, and optionally stretchable, at least on the side that is in contact with the body. The material that contacts the body also preferably slows the cooling of the body part to avoid damage by overcooling, e.g., frostbite. The material should allow heat to flow from the injured body part. Preferably, the material does not allow heat to flow through it at a rate that will result in frostbite. The desired effect is cooling without freezing and the cooling is preferably at a rate that creates no more pain than can be withstood by the user and which does not cause damage to the treated area.

Typically the outer cover has two faces or sides that join together at the edges to form a sac or pouch structure having one open end and three closed edges. The edges of the outer cover can be sealed by sewing, gluing, heat sealing, or the like, or can be integral, e.g., when formed from tubular material that requires no sealing on the side edges. Typically the two faces or sides of the outer cover have about the same dimension and form a more or less flat sac or pouch. In a preferred embodiment, the two faces or sides of the outer cover have different dimensions, with the face coated with the adhesive layer and/or strips having a narrower size, and the face without the adhesive being wider. The two faces join together at the closed edges with the narrower face taking a more or less flat configuration, while the wider face taking a protruding or bulging configuration to form one or more bulging interior compartments to contain one or more inner cooling packs, as is illustrated in FIG. 5, FIG. 11, and FIG. 17. The flat configuration of the face coated with adhesive improves the adhesion of the ice bag device to the garment surface.

The outer cover can most conveniently have one compartment designed to have dimensions suitable to hold one inner cooling pack comprising an at least relatively liquid impermeable inner container containing a cooling medium. The inner cooling pack can be inserted into the compartment through the open end of the outer cover. The inner cooling pack is preferably composed of a resealable or permanently sealed plastic liquid impermeable inner container to contain a cooling medium, wherein said cooling medium is preferably either ice, ice and water combination, water, refrigeratable cooling gel, or endothermic chemical cooling system. Ice, and ice and water mixture are preferably contained in a resealable or reclosable plastic container, such as a reclosable zipper bag, which is conveniently either a commercially available reclosable zipper bag such as a sandwich or freezer zipper bag, as described hereinafter, or a specially made zipper bag of any suitable size and thickness. The use of a reclosable bag allows one to replace the cooling medium when it is no longer cool. A refrigeratable cooling gel and/or an endothermic chemical cooling system are preferably contained in permanently sealed plastic containers. The permanently sealed plastic container can also contain liquid water to be placed in, e.g., a conventional freezer to form ice for use in the method and/or article of the present invention. In this embodiment, provision should be made for the expansion of the water when it freezes, either by having sufficient void space or by making the container expansible.

The outer cover can also be divided into two or more compartments to hold two or more inner cooling packs. The preferred multi-compartment outer cover has two or three compartments, more preferably two compartments, especially for compact size inner cooling packs. An ice bag device of the present invention having multiple compartments has the advantage of distributing solid cooling media such as ice chips or ice cubes more evenly on the skin surface, and better preventing the ice from accumulating into one area, thus providing more even cooling and/or comfort. The outer cover is conveniently separated into two or more compartments, preferably of approximately equal size, by divider sewn lines, glue lines or staple lines that are stitched or otherwise added into the outer cover. A non-limiting example of an outer cover having two compartments is depicted in FIG. 11.

Preferably the compartment(s) of a multi-compartment outer cover have dimensions that can accommodate/fit the reclosable inner cooling packs comprising commercially available plastic zipper containers of the quart size or sandwich size as described hereinafter. A preferred multi-compartment outer cover has compartments that can hold inner cooling containers that are commercially available reclosable snack bags, as described hereinafter.

Another aspect of this invention relates to a non-constrictive adhesive ice bag device that can be attached to a garment, said ice bag device comprising:

(a) an outer cover having one face covered at least partially with mounting adhesive as described hereinabove; and (b) one or more preferably plastic, preferably reclosable, liquid impermeable inner containers, preferably rectangular or square in shape, containing cooling media such as ice cubes, ice chips, crushed ice, or ice and water mixture, to form inner cooling packs, or ice bags, wherein said inner cooling packs can fit inside the enclosure of the outer cover, and wherein each said inner container is closed, e.g., sealed, on three sides and has the fourth side open, preferably having a reclosable closure, more preferably a rib and groove sealing closure (zipper closure); and wherein the optional ice-filled inner cooling pack(s) of (b) can optionally be replaced by chilled or frozen gel pack(s) and/or chemical cold pack(s), when said pack(s) are available.

An alternative embodiment of the present invention relates to the non-constrictive ice bag device hereinabove, wherein the outer cover is not self-adhesive, and the adhesive layer is provided separately as adhesive tape, such as bandage adhesive tape or adhesive bandage strips.

In particular, this invention relates to an assemblage of elements, comprising an outer cover as disclosed herein and one or more zipper bags, and adhesive tape when the outer cover is not self-adhesive, that can be used to create an ice bag device, that is compact, e.g., can fit in a first-aid box along with other first-aid items, to be used at home or away from home, e.g., in sporting events, such as at a soccer field or a basketball court, in other outings such as hikes or picnics, and/or on trips. Such elements are preferably easy to be manufactured and/or inexpensive.

Optionally, but not as preferred, the ice bag device of the present invention can be attached directly to the skin. An ice bag device comprising a self-adhering outer cover of closed sack structure, especially an outer cover with extended peripheries covered with a mounting adhesive layer, containing one or more permanently sealed aqueous or endothermic chemical inner cooling packs is not preferred. The attachment of such ice bag device to the skin is especially not preferred.

A preferred inner container is constructed of a liquid impermeable, e.g., waterproof synthetic "plastic" material such as a polyethylene film. Such inner container preferably is a reclosable zipper bag which is closed (e.g., sealed) on three sides and has the fourth side open but preferably having a reclosable closure, preferably an interlocking rib and groove, or male and female sealing closure, as described, e.g., in U.S. Pat. Nos. 3,338,284 issued Aug. 29, 1967 to Ausnit; 4,263,079 issued Apr. 21, 1981 to Sutrina et al.; 4,363,345 issued Dec. 14, 1982 to Scheibner; 4,829,641 issued May 16, 1989 and 4,907,321 issued Mar. 13, 1990, both to Williams; 5,009,828 issued Apr. 23, 1991 to McCree; 5,070,584 issued Dec. 10, 1991 to Dais et al.; 5,140,727 issued Aug. 25, 1992 to Dais et al.; 5,647,100 issued Jul. 15, 1997 to Porchia et al.; and the references cited therein.

Preferred inner containers are rectangular or square in shape. Each inner container can be defined by two sets of dimensions, namely, the outer dimension that includes the sealing closure line or part, and the inner dimension that counts only the storage area, without the sealing closure part. Each dimension is typically defined by two sides, the first side is the lateral or opening side and the second side is the vertical closed side. In use, the inner container(s) can be filled with, e.g., ice cubes, ice chips, crushed ice, or ice and water mixture, then the resealable closure is firmly pressed along the sealing closure line in order to hermetically seal the resulting inner cooling pack(s) or ice bag(s). Preferably the sealing closure part is folded back onto one side of the inner zipper bag before the inner bag is placed in a compartment of the outer cover, in order to maximize the cold contact surface and/or to better maintain the seal against any accidental opening due to pressure applied on the side of the ice bag device.

Preferred reclosable inner containers for use in the ice bag device of the present invention are the commercially available household reclosable plastic zipper bags for use as food containers or freezer storage bags, and sold, e.g., under the brand names Ziploc® or Glad®, or store name, e.g., Kroger®, and the like. The preferred commercially available household zipper bags for use in an outer cover that has one compartment are the quart size bags (typically having an outer dimension of from about 17 cm×21.5 cm to about 18.5 cm×23 cm, and an inner dimension of from about 17 cm×19.5 cm to about 18.5 cm×21 cm) or the sandwich bags (typically having an outer dimension of from about 16 cm×18.5 cm to about 17 cm×18.5 cm, and an inner dimension of from about 16 cm×14 cm to about 17.5 cm×16 cm). The preferred commercially available household zipper bags (or inner containers) for use in an outer cover that has more than one compartment are the sandwich bags (typically having an outer dimension of from about 16 cm×18.5 cm to about 17 cm×18.5 cm, and an inner dimension of from about 16 cm×14 cm to about 17.5 cm×16 cm) or the snack size bags (typically having an outer dimension of from about 16 cm×9 cm to about 17 cm×11.5 cm, and an inner dimension of from about 16 cm×7.5 cm to about 17 cm×9 cm). Industrial zipper bags of many sizes are also available, e.g., from Lab Safety Supply, Inc., Janesville, Wis.

The inner zipper containers can be made of plastic film, preferably transparent plastic film. One common material used in the household and industrial zipper bag is polyethylene. The zipper bags that are useful as inner containers of the present invention typically have a film thickness of from about 0.01 mm to about 0.25 mm, preferably from about 0.02 mm to about 0.15 mm, more preferably from about 0.02 mm to about 0.1 mm, and even more preferably from about 0.03 mm to about 0.08 mm.

The outer cover can optionally be used to hold and apply other cold media in place of the ice-filled inner cooling pack. Non-limiting examples of such cold media include a pre-cooled gel pack, or a chemical cold pack. A cold gel pack is a refrigeratable gel cold pack that comprises a refrigerant or coolant gel material contained in a permanently sealed plastic housing which can be either flexible or relatively inflexible. The gel packs are stored in, e.g., a conventional household freezer for chilling or cooling and are then ready for use. Non-limiting examples of cold gel packs and/or coolant compositions are given in U.S. Pat. Nos. 3,780,537 issued Dec. 25, 1973 and 3,885,403 issued May 27, 1975, both to Spencer, and 5,148,804 issued Sep. 22, 1992 to Hill et al. Many commercially available gel packs, such as the Nexcare™ First Aid Reusable Cold Pack produced by 3M Health Care, St. Paul, Minn., Ace® Brand Cold Compress Reusable and Ace Brand Hot & Cold Compress Reusable distributed by BD Consumer Healthcare, Franklin Lakes, N.J., are elongated in dimension with sizes of from about 23 cm×9.5 cm to about 27 cm×12.5 cm. When they are stored in a household freezer, they are chilled but not frozen. They can be folded in two in order to be placed in a compact outer cover with one compartment of the present invention that is designed to accommodate one sandwich zipper bag. Preferably they can be used in an elongated outer cover that is designed to accommodate the elongated gel packs.

A chemical cold pack typically comprises an endothermic chemical system comprising different chemicals which, when mixed together, undergo an endothermic reaction to reduce the temperature of the cold pack. Typically, the different chemicals are contained in separate compartments to prevent a premature reaction. The chemical cold pack is "activated" when the compartments are, e.g., connected by a certain means so that the chemicals are mixed to produce the endothermic reaction. An example of such endothermic chemical system is dry ammonium nitrate and water. Other non-limiting examples of endothermic chemical systems and/or chemical cold packs are given in U.S. Pat. Nos. 2,882,692 issued Apr. 21, 1959, 2,898,744 issued Aug. 11, 1959, 3,058,313 issued Oct. 16, 1962, all to Robbins; 2,925,719 issued Feb. 23, 1960, to Robbins et al.; 3,643,665 issued Feb. 22, 1972 to Caillouette; 3,893,834 issued Jul. 8, 1975 to Armstrong; 4,986,076 issued Jan. 22, 1991 to Kirk et al.; and 5,545,197 issued Aug. 13, 1996, 5,792,213 issued Aug. 11, 1998, 5,967,308 issued Oct. 19, 1999, and 6,036,004 issued Mar. 14, 2000, all to Bowen.

The present invention also relates to a method for first aid treatment of injuries by using adhesive to temporarily attach an ice bag device comprising an outer cover holding a cooling pack, such as an ice bag or cooling gel pack to a garment, and to thereby apply said cooling pack to an injured body part when the garment is worn. The present invention optionally further relates to a method of using adhesive to close the opening of the outer cover of said ice bag device. This method is of great value, since in general it permits one to carry/store only the described outer cover, and the optional empty inner containers, e.g., empty plastic zipper bags, as separate items, yet permitting the fabrication and use of a non-constrictive ice bag device readily and immediately when it is needed.

The present invention also relates to a method for first aid treatment of injuries by using adhesive to temporarily attach an ice bag device of the present invention directly to the skin surface of the user, to apply said cooling bag device to an injured body part, said ice bag device preferably comprising an outer cover having a sac structure with an open end, two or more extended peripheries with only said extended peripheries being covered with mounting adhesive, and said cover holding one or more cooling bags, such as an ice bag or cooling pack.

Alternatively, the method provides first aid treatment of injuries by using preferably separate adhesive tape, preferably bandage adhesive tape, to temporarily attach an ice bag device of the present invention directly to the skin surface of the user, to apply said cooling bag device to an injured body part, said ice bag device preferably comprising an outer cover having a sac structure with an open end, said cover holding one or more cooling bags, such as an ice bag or cooling pack, and wherein said cover is not a self-adhering cover.

The present invention also relates to an alternative method to create an ice bag device, e.g., in the case there is more than one bruise and there are insufficient outer covers. In one embodiment it relates to the option of using common bandage adhesive first aid tape of the type found in most first aid kits to attach a cooling pack itself when the outer cover is not available, directly to a garment, or, less desirably, the skin. In a preferred embodiment, the method comprises the steps of using one or more long strips of bandage adhesive first aid tapes to attach the inner cooling pack itself to a garment. The first aid strips are to be attached to one side the zipper bag in the way there is enough exposed tape for use to attach the ice bag to a garment. Preferably, the method comprises the use of an ice-filled zipper bag and the first aid tape strips, to be attached, preferably on a outside of the garment. It is preferable to attach the adhesive tape to the empty and dry zipper bag first, before it is filled with ice, to avoid its surfaces to be wetted by potential water condensation that can reduce the tape adhesion to the zipper bag. Alternatively, the zipper bag can be filled with ice first, before the tape strips are attached to its surface, but the user should take the precaution to wipe dry any water condensation that may occur. While this can be effective for cooling, it is desirable to suggest placing something between the cooling pack and the skin to avoid overcooling. In another embodiment, the present invention relates to the option of using double-sided adhesive tape to attach a cooling pack directly to the garment, or, less desirably, the skin. The method comprises the step of attaching one side of the double-sided adhesive tape strips to the cooling pack, and the step of using the other side of the double-sided adhesive tape to attach the ice bag to a garment.

The present invention also relates to an article of manufacture comprising one or more outer covers as described hereinabove, optionally adhesive tape if the cover(s) do not have adhesive strips attached, and optionally at least one other element which is: one or more empty reclosable relatively liquid-impermeable plastic containers, or sealed, liquid impermeable plastic containers containing a cooling medium such as water, refrigeratable cooling gel, or endothermic chemical system, preferably one or more empty reclosable zipper containers, to contain a cooling medium, that can fit inside the enclosure of the outer cover; and/or a sealed plastic wrapper to keep the outer cover(s) and the optional inner container(s) in a hygienic, non-contaminated condition in storage and/or to prevent accidental loss of one or more of the elements, wherein the plastic wrapper can be transparent or opaque, and can be white or colored; and/or said article is optionally but preferably packaged in association with a set of instructions for use to direct the consumer to use the product properly, to ensure that the consumer knows what benefits can be achieved, and how best to obtain these benefits. The outer cover is preferably transparent or marked with the contents so that the article can be readily identified in an emergency.

The present invention also relates to the association of instructions for use with the outer cover, the ice bag device, the method, or the article of manufacture described hereinabove to ensure that the method can be practiced and the cover and/or the article be used efficiently, quickly, and effectively so as to maximize the effect of the cooling treatment on an injury. The set of instructions provides the information on how to use the outer cover, the inner containers, and the cooling media such as ice, as well as the cooling gel or the chemical cooling pack, to create a convenient non-constrictive ice bag device that provides immediate cooling to an injury.

The set of instructions of the present invention preferably includes one or more of the following instructions: to direct the consumer to place the outer cover on a location on a garment such that the contained cooling medium will be in close contact with the injured area of the body when the garment is worn, with the outer cover placed either to the inside of the garment if there is room inside the garment to fit the complete ice bag device and/or if the garment is composed of a thick layer, such as a jacket, or to place the outer cover on the outside of the garment if the garment is made of thin material that allows good transmission of heat from the injured body part, and/or if there is not enough room inside the garment, such as a pair of tight pants or a sock, then to attach the outer cover to the garment using the adhesive layer, with the open end oriented on top, preferably, to facilitate the insertion of one or more inner cooling packs comprising containers containing a cooling medium if the said cooling packs are not already inside the outer cover when it is attached to the garment.

The set of instructions preferably also includes instructions to direct the consumer to fill the inner container(s) with cooling media such as ice cubes, ice chips or crushed ice, then to seal the filled inner container(s), then, optionally, but preferably, to fold the sealing closure back against one side of the inner container, then to place the filled inner ice bag(s) in the compartment(s) of the outer cover.

The set of instructions can include an instruction to direct the consumer to precool one or more gel packs, or to activate one or more chemical cool packs, for use as the inner cooling packs.

The set of instructions preferably includes an instruction to direct the user to wear the garment so as to apply the resulting attached ice bag device over the injured body part where cooling can occur.

The set of instructions can include an instruction to direct the consumer to a source of ice or cold fluid, preferably including a home refrigerator, ice boxes or coolers for beverages at a sport game, and/or a fast food restaurant and/or hotel or motel when one is on a trip. There is usually some ice or cold water or other cold fluid available at sporting events.

The set of instructions can include an instruction to direct the consumer to optionally use already cooled gel pack(s) or chemical cooling pack(s) in the place of the ice-filled inner cooling pack(s). The set of instructions can also include an instruction to direct the consumer to keep the article of the present invention readily available, e.g., in their first-aid kit. The set of instructions can include an instruction disclosing the non-constrictive nature and/or benefit of the ice bag device of the present invention as compared to other ice bag devices that have strapping. The instructions can also contain a suggestion to pre-cool the injured body part by direct application of the cooling medium, cool pack, etc. to the skin followed by the application to a garment for an effective, longer term follow up treatment. The set of instructions preferably comprises one or more of the hereinabove instructions.

The set of instructions can optionally disclose an alternative method to create an ice bag device in the case there is more than one bruise and there are insufficient outer covers. For example, the option of using common adhesive first aid tape of the type found in most first aid kits to attach a cooling pack directly to the garments, or, less desirably, the skin. In a preferred embodiment, the method comprises the steps of: (a) cut one or more long strips of first aid tapes and attach them to one side of an empty plastic zipper bag in a way where there is enough exposed tape for use to attach the zipper bag to a garment, (b) fill the zipper bag with ice and seal the ice-filled zipper bag, (c) place the ice-filled zipper bag on a location, preferably on a outside of a garment such that the ice-filled zipper bag is in close contact with the injured area of the body when the garment is worn, and attach the zipper bag to that garment using said tape. It is preferable to attach the tape to the empty and dry zipper bag first, before it is filled with ice, to avoid its surfaces to be wetted by potential water condensation that can reduce the tape adhesion to the zipper bag. Alternatively, the zipper bag can be filled with ice first, before the tape strips are attached to its surface, but the user should take the effort to wipe dry any water condensation that may occur. While this can be effective for cooling, it is desirable to suggest placing something between the cooling pack and the skin to avoid overcooling. Also, while such tape can be effective to hold the cooling pack in place, it can cause unacceptable stains on garments, so providing sufficient outer covers is still preferred. These alternative instructions are very important where the caregiver will typically be unused to providing emergency aid.

The set of instructions can be printed, e.g., on one or more of: the package, the wrapper, an accompanying instruction flyer or booklet, and/or communicated via print and/or electronic mass media, e.g., newspapers, magazines, radio, television, internet, circulars, etc., to members of sport and/or outdoor organizations, and the like.

The instructions can be in one or more languages. The instructions can be in words, or illustrative images and/or icons preferably in combination with words. It is preferable to have the instructions contain pictorial representations of the steps in preparing and using the ice bag device to supplement, or replace the written instructions when the user is not familiar with the language(s) of the instructions.

This invention further relates to an outer cover, an ice bag device and/or an article of manufacture comprising said outer cover and other elements of the ice bag device of the present invention, wherein one or more of the outer cover, the inner container(s) or bag(s), the wrapper, the package, and/or the set of instructions carry indicia showing, e.g., a logo, emblem, symbol, motif, sign, figure, mark, icon, pictogram, insignia, design, image, description, and/or advertisement for, e.g., a sport league, sport franchise, sport sponsor, non-profit or governmental organization, and/or for-profit commercial or industrial organization. The use of such indicia provides a measure of assurance to the user that the device is useful and not harmful, especially when the instructions are followed.

The above use of indicia can be used as part of the method of doing business in which the use of the device, the outer cover, etc., are promoted by using one or more existing associations, businesses, etc., to make, distribute, or recommend the ice bag device, the outer cover, and/or the method to provide assurance to the intended user that the device is acceptable for the intended result. Since the primary benefit of the invention is to obtain fast treatment of trauma to diminish the damage to the individual, it follows that the user will normally not be a medical professional, and often will not have even basic first aid skills. It is important that these individuals know that the ice bag device is safe and effective and that the instructions are safe when followed, and have access to basic instructions for use.

This invention relates to the method of doing business wherein the outer cover, other elements of the ice bag device and/or the article of manufacture comprising said outer cover and other elements of the ice bag device of the present invention, are distributed with the approval of one or more entities having an association with individuals that are likely to be injured and need an ice bag device on an urgent basis, such as an amateur or professional athletic association and/or optionally, attaching the indicia of at least one of said entities to said article and/or associating said indicia with said article.

Specific embodiments are described hereinafter with reference to the drawings:

FIGS. 1 and 3 are two views of a self-adhesive, non-constrictive ice bag device of the present invention, designated as 101 and comprising the flexible outer cover 103. FIG. 1 is a plan view of the outer cover with a portion of the cover being partly cut away to show the inner plastic zipper container shown thereafter as FIG. 2. FIG. 3 is a cross-sectional view of the ice bag device 101 taken along the line 3—3. FIG. 4 is an oblique exploded view of the outer cover 103. The outer cover 103 has a sac structure having face (side) 105 and face 107. The outer cover is joined along the periphery on three sides to form three closed edges 112, 113, and 114, and an open end 111 with two edges 125 and 127, which together define the cover interior 129. A layer of mounting adhesive 145 is positioned on top and covers the whole surface of face 105. Release paper sheet 155 covers the adhesive layer 145 to protect the adhesive from prematurely sticking to a surface other than the intended user's garment. In use, the release paper 155 is removed to expose the adhesive layer 145, as shown in FIG. 4, to affix the ice bag device 101 comprising the outer cover 103 containing the ice bag (inner zipper container) 81 to the surface of a garment at a location that is in close contact with the injured area of the user. FIG. 1 also shows the outer cover 103 partly cut away to show a water-impermeable inner plastic zipper container 81 with a reclosable, interlocking rib and groove sealing closure 83, and filled with ice chips 85. The cut away also shows part of the underlying face 105, part of the adhesive layer 145, and part of face 107. FIG. 2 is a plan view of the isolated water-impermeable inner plastic zipper container 81, with the reclosable sealing closure 83, and containing ice chips 85, that is to be placed in the cover interior compartment 129 of the outer cover 103.

FIG. .5 is a cross-sectional view of a preferred version of the ice bag device 101, taken along the line 3—3, and designated as 1101, comprising an improved outer cover 1103, as compared to and corresponding to the ice bag device 101 and the outer cover 103 of FIG. 3. In the outer cover 1103, face 1107 is wider that face 1105. Face 1105 and face 1107 join at edges 1112 and 1114, with face 1105 taking a flatter configuration and face 1107 taking a protruding or bulging configuration, to form a bulging interior compartment 1129 to contain the inner zipper container 81 which is filled with ice chips 85. A layer of mounting adhesive 1145 is positioned on top and covers the whole surface of the more or less flat face 1105. Release paper sheet 1155 covers the adhesive layer 1145 to protect the adhesive from prematurely sticking to a surface other than the intended user's garment. In use, the release paper 1155 is removed to expose the adhesive layer 1145 to affix the ice bag device 1101 containing the inner zipper container 81 to the surface of a garment at a location that is in close contact with the injured area of the user. The flat configuration of face 1105 and of the adhesive layer 1145 improves the adhesion of the ice bag device 1101 to the garment surface and/or the cooling effect.

FIG. 6 is a plan view of an alternative embodiment of the self-adhering outer cover of the present invention, designated as 603 with a sack structure having one open end 611, three closed edges 612, 613, and 614, and two adhesive strips 641 and 643. The adhesive strip 641 is located close to the open end 611 of the outer cover, and the adhesive strip 643 is located at the opposite closed edge 613. In turn, the adhesive strips 641 and 643 are covered with the two release paper strips 651 and 653. In between the two adhesive strips is the exposed area 609 of face 605 of the outer cover 603. In FIG. 6 a portion of the release paper strips 651 and 653 and a portion of the adhesive strips 641 and 643 are broken away to show part of the underlying face 605, and part of the adhesive strips 641 and 643.

FIG. 7 is a plan view of an alternative embodiment of the self-adhering outer cover of the present invention, designated as 703 with a sack structure having one open end 711, three closed edges 712, 713, and 714, and two adhesive strips 742 and 744. Adhesive strip 742 is located close to the closed end 712 of the outer cover, and the adhesive strip 744 is located at the opposite closed edge 714. In turn, the adhesive strips 742 and 744 are covered with the two release paper strips 752 and 754. In between the two adhesive strips is the exposed area 709 of face 705 of the outer cover 703. In FIG. 7 a portion of the release paper strips 752 and 754 and a portion of the adhesive strips 742 and 744 are broken away to show part of the underlying face 705, and part of the adhesive strips 742 and 744.

FIG. 8 is a plan view of an alternative embodiment of the self-adhering outer cover of the present invention, designated as 803 with a sack structure having one open end 811, three closed edges 812, 813, and 814, and a four-sided adhesive strip 845 that borders all the four edges of face 805 of the outer cover 803. In turn, adhesive strip 845 is covered with the four-sided release paper strip 855. In the middle of the adhesive strip 845 is an exposed area 809 of face 805 of the outer cover 803. In FIG. 8 portions of the release paper strip 855 and portions of the adhesive strip 845 are broken away to show part of the underlying face 805, and parts of the adhesive strip 845. The release paper strip 855 can optionally be replaced by two or more shorter release paper strips, each covering one portion of the adhesive strip 845, for an easier removal of the release paper strips, providing that these shorter release paper strips still cover the entire surface of the adhesive strip 845.

FIGS. 9 and 10 are two views of an alternative embodiment of the self-adhering ice bag device of the present invention, designated as 901, comprising the outer cover 903 that contains an inner zipper container 81 containing ice 85. FIG. 9 is a plan view of the ice bag device 901. FIG. 10 is a cross-sectional view of the ice bag device 901 taken along the line 10—10. The outer cover 903 has a sack structure having face 905 and face 907, open end 911, three closed edges 912, 913, and 914, and two extended peripheries 962 and 964 that are extensions from the closed edges 912 and 914. The extended peripheries 962 and 964 are covered with mounting adhesive layers 942 and 944 that are on the same side as face 905. In turn, the adhesive layers 942 and 944 are covered with the release paper strips 952 and 954. In use, the release paper strips 952 and 954 are removed to expose the adhesive strips 942 and 944 to affix the ice bag device 901 containing the ice bag 81 to the surface of a garment at a location which is in close contact with the injured area of the user. FIG. 9 also shows the outer cover 903 partly cut away to show the inner plastic zipper container 81 filled with ice chips 85, and part of face 907. In FIG. 9 a portion of the release paper strips 952 and 954 and a portion of the adhesive strips 942 and 944 are also broken away to show part of the underlying extended peripheries 962 and 964, and part of the adhesive strips 942 and 944.

FIG. 11 is a cross-sectional view of a preferred version of the ice bag device 901, taken along the line 10—10, and designated as 1901, comprising an improved outer cover 1903, as compared to and corresponding to the ice bag device 901 and the outer cover 903 of FIG. 10. In the outer cover 1903, face 1907 is wider that face 1905. Face 1905 and face 1907 join at edges 1912 and 1914, with face 1905 taking a flatter configuration and face 1907 taking a protruding or bulging configuration, to form a bulging interior compartment 1929 to contain the inner zipper container 81 which is filled with ice chips 85. The two extended peripheries 1962 and 1964, which are extensions from the closed edges 1912 and 1914, are covered with mounting adhesive layers 1942 and 1944 that are on the same side as face 1905. Release paper strips 1952 and 1954 cover the adhesive layers 1942 and 1944 to protect the adhesive from prematurely sticking to a surface other than the intended user's garment. In use, the release papers 1952 and 1954 are removed to expose the adhesive layers 1942 and 1944 to affix the ice bag device 1901 containing the inner zipper container 81 to the surface of a garment at a location that is in close contact with the injured area of the user. The flat configuration of face 1905 improves the adhesion of the ice bag device to the garment surface and/or the cooling effect.

Figure 13:
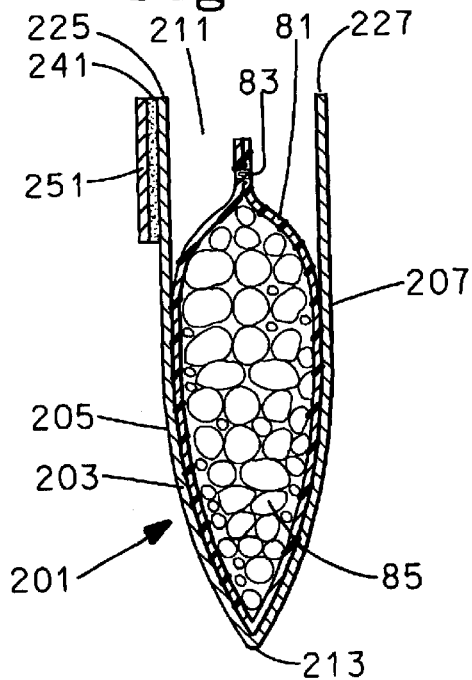
FIG. 13 is a cross-sectional view of the ice bag device of FIG. 12 taken along the line 13—13.

FIGS. 12 and 13 are two views of an alternative embodiment of the self-adhering ice bag device of the present invention, designated as 201, comprising the outer cover 203 that contains an inner zipper container 81 with a reclosable, interlocking rib and groove sealing closure 83 and filled with ice 85. FIG. 12 is a plan view of the ice bag device 201. FIG. 13 is a cross-sectional view of the ice bag device 201 taken along the line 13—13. The outer cover 203 has a sack structure having face 205 and face 207, three closed edges 212, 213, and 214, and open end 211 with two edges 225 and 227. The outer cover 203 also has the mounting adhesive strip 241 and two extended peripheries 262 and 264 that are extensions from the closed edges 212 and 214. The adhesive strip 241 is located close to the open end 211 on face 205 of the outer cover. The extended peripheries 262 and 264 are covered with mounting adhesive strips 242 and 244 that are on the same side as face 205. In turn, the adhesive strips 241, 242 and 244 are covered with the release paper strips 251, 252 and 254. In use, the release paper strips 251, 252 and 254 are removed to expose the adhesive strips 241, 242 and 244 to affix the ice bag device 201 containing the ice bag 81 to the surface of a garment at a location that is in close contact with the injured area of the user. FIG. 12 also shows the outer cover 203 partly cut away to show the inner plastic zipper container 81 which is filled with ice chips 85. The cut away also shows part of the underlying face 205, part of the adhesive layer 241, and part of face 207. In FIG. 12 a portion of the release paper strips 252 and 254 and a portion of the adhesive strips 242 and 244 are also broken away to show part of the underlying extended peripheries 262 and 264, and part of the adhesive strips 242 and 244. In this embodiment, the outer cover is not closed, so it is important that the cover be placed so as to keep the open end pointed up.

Figure 15:
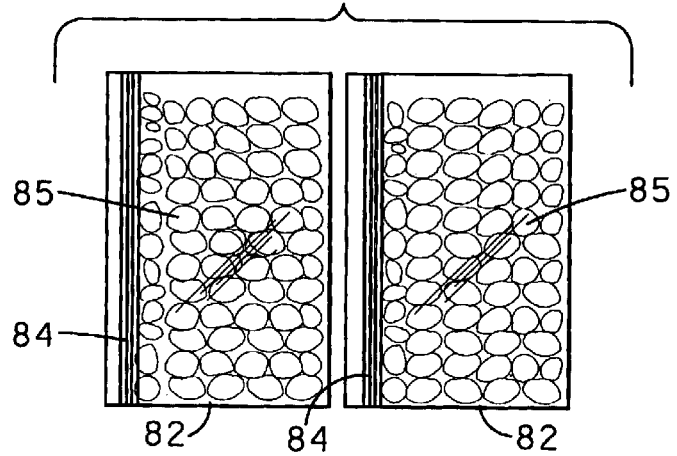
FIG. 15 is a plan view of the two isolated zipper containers filled with ice chips of the ice bag device of FIG. 14.
Figure 14:
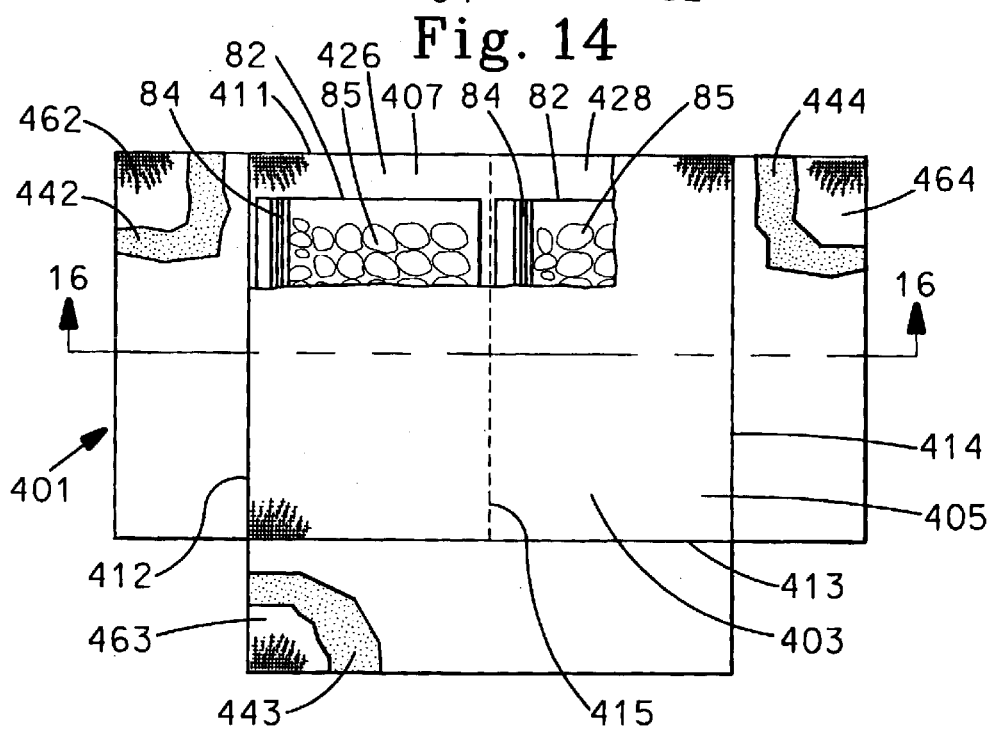
FIG. 14 is a plan view of an alternative embodiment of the self-adhering ice bag device of the present invention, comprising an outer cover with a sack structure having two compartments, two open ends on one edge, and three extended peripheries covered with mounting adhesive, and containing two resealable plastic zipper containers containing ice chips, said outer cover being partly cut away to show-said ice-filled zipper containers.
Figure 16:
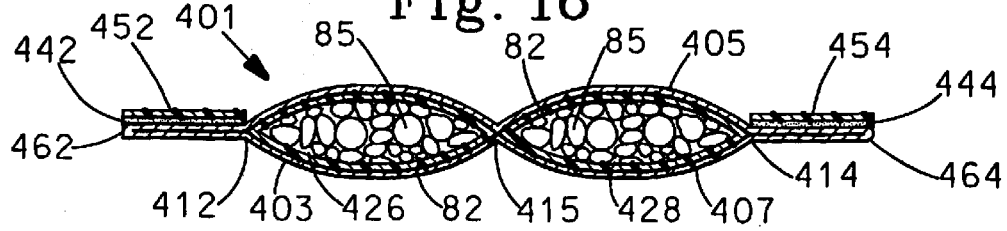
FIG. 16 is a cross-sectional view of a version of the ice bag device of FIG. 14 taken along the line 16—16.

FIGS. 14 and 16 are two views of an alternative embodiment of the self-adhering ice bag device of the present invention, designated as 401, comprising the outer cover 403 containing two inner zipper containers 82. FIG. 14 is a plan view of the ice bag device 401. FIG. 16 is a cross-sectional view of the ice bag device 401 taken along the line 1616. The outer cover 403 has a sack structure having face 405 and face 407, three closed edges 412, 413, and 414, and an open end 411. The outer cover 403 is separated into two interior compartments 426 and 428 of approximately equal size by a sewn line, glue line or staple line that is stitched or formed along the divider line 415. FIG. 14 also shows the outer cover 403 partly cut away to show part of the two water-impermeable inner plastic zipper containers 82 which are placed in the cover interior compartments 426 and 428, wherein each container 82 has a reclosable, interlocking rib and groove sealing closure 84, and is filled with ice chips 85. The partial cut away also shows a part of face 407. FIG. 15 is a plan view of the two isolated zipper containers 82 of the ice bag device 401 of FIG. 14, each with a reclosable, interlocking rib and groove sealing closure 84, and filled with ice chips 85. The outer cover 403 also has three extended peripheries 462, 463, and 464 that are extensions from the closed edges 412, 413, and 414, respectively. The extended peripheries 462, 463, and 464 are covered with mounting adhesive strips 442, 443, and 444 that are on the same side as face 405. In turn, the adhesive strips 442, 443 and 444 are covered with the release paper strips 452, 453 and 454, respectively. In use, the release paper strips 452, 453 and 454 are removed to expose the adhesive strips 442, 443 and 444 to affix the ice bag device 401 containing the ice bags 82 to the surface of a garment at a location that is in close contact with the injured area of the user. In FIG. 14 a portion of the release paper strips 452, 453 and 454 and a portion of the adhesive strips 442, 443 and 444 are also broken away to show part of the underlying extended peripheries 462, 463 and 264, and part of the adhesive strips 442, 443 and 444.

FIG. 17 is a cross-sectional view of a preferred version of the ice bag device 401, taken along the line 16—16, and designated as 1401, comprising an improved outer cover 1403, as compared to and corresponding to the ice bag device 401 and the outer cover 403 of FIG. 16. In the outer cover 1403, face 1407 is wider that face 1405. Face 1405 and face 1407 join at edges 1412 and 1414, and at the divider line 1415, with face 1405 taking a flatter configuration and face 1407 taking a protruding or bulging configuration, to form two bulging interior compartments 1426 and 1428 to contain the two inner zipper containers 82 which is filled with ice chips 85. The two extended peripheries 1462 and 1464 which are extensions from the closed edges 1412 and 1414, are covered with mounting adhesive layers 1442 and 1444 that are on the same side as face 1405. Release paper strips 1452 and 1454 cover the adhesive layers 1442 and 1444 to protect the adhesive from prematurely sticking to a surface other than the intended user's garment. In use, the release papers 1452 and 1454 are removed to expose the adhesive layers 1442 and 1444 to affix the ice bag device 1401 containing the inner zipper containers 82 to the surface of a garment at a location that is in close contact with the injured area of the user. The flat configuration of face 1405 improves the adhesion of the ice bag device to the garment surface and/or the cooling effect.

FIGS. 18 and 19 are two views of an alternative embodiment of the self-adhering ice bag device of the present invention, designated as 301, comprising the outer cover 303 that contains an inner zipper container 81 with a reclosable, interlocking rib and groove sealing closure 83 and filled with ice 85. FIG. 18 is a plan view of the ice bag device 301. FIG. 19 is a cross-sectional view of the ice bag device 301 taken along the line 19—19. The outer cover 303 has a sack structure having face 305 and face 307, three closed edges 312, 313, and 314, and an open end 311 with two edges 325 and 327. The outer cover 303 also has the extended periphery 361 that is an extension from the open edge 325 and the extended periphery 363 that is an extension from the closed edge 313. The extended peripheries 361 and 363 are covered with mounting adhesive layers 341 and 343 that are on the same side as face 305. In turn, the adhesive layers 341 and 343 are covered with the release paper strips 351 and 353. In use, the release paper strips 351 and 353 are removed to expose the adhesive strips 341 and 343 to affix the ice bag device 301 containing the ice bag 81 to the surface of a garment at a location that is in close contact with the injured area of the user. FIG. 18 also shows the outer cover 303 partly cut away to show the inner plastic zipper container 81 filled with ice chips 85, and part of face 307. In FIG. 18 a portion of the release paper strips 351 and 353 and a portion of the adhesive strips 341 and 343 are broken away to show part of the underlying extended peripheries 361 and 363, and part of the adhesive strips 341 and 343. Since the outer cover is open at one end, that end should be kept at the top of the device when it is attached to a garment.

FIGS. 20, 21, and 22 are three different views of an alternative embodiment of the self-adhering ice bag device of the present invention, designated as 501, comprising the outer cover 503 that contains an inner zipper container 81 with a reclosable, interlocking rib and groove sealing closure 83 and containing ice chips 85. FIG. 20 is a plan view of the ice bag device 501. FIG. 21 is a cross-sectional view of the ice bag device 501 taken along the line 21—21. FIG. 22 is a cross-sectional view of the ice bag device 501 taken along the line 22—22. The outer cover 503 has a sack structure having face 505 and face 507, three closed edges 512, 513, and 514, and an open end 511 with two edges 525 and 527. The outer cover 503 also has four extended peripheries 561, 562, 563, and 564 that are extensions from the four edges 525, 512, 513, and 514, respectively. The extended peripheries 562, 563, and 564 are covered with mounting adhesive layers 542, 543, and 544 that are on the same side as face 505. The extended periphery 561, on the other hand, has an adhesive layer 541 that is positioned on the opposite side as face 505 (that is, the adhesive layer 541 is on the same side as face 507). Similar to other ice bag devices hereinabove, the adhesive layers 541, 542, 543, and 544 are covered with release paper strips 551, 552, 553, and 554, respectively. In use, the release paper strip 551 is removed to expose the adhesive layer 541, and the extended periphery 561 is folded and the adhesive layer 541 is pressed on the edge 527 to enclose the ice bag 81 and used as a closure means to keep the ice bag 81 inside the outer cover 503. Release paper strips 552, 553, and 554 are also removed to expose the adhesive strips 542, 543, and 544 to affix the ice bag device 501 containing the ice bag 81 to the surface of a garment at a location which is in close contact with the injured area of the user. FIG. 20 also shows the outer cover 503 partly cut away to show the inner plastic zipper container 81 with reclosable closure 83 and filled with ice chips 85, and part of face 507. In FIG. 20 a portion of the release paper strips 552, 553, and 554, and a portion of the adhesive strips 542, 543, and 544 are broken away to show part of the underlying extended peripheries 562, 563, and 564, and part of the adhesive strips 542, 543, and 343. Similarly, FIG. 20 also shows the extended periphery 561 partly broken away to show part of the underlying adhesive strip 541 and part of the release paper strip 551.

For the ice bag devices, e.g., 101, 201, 301, 401, 501, 901, 1101, 1401, and/or 1901 hereinabove, the ice packs 81 and/or 82 can optionally be replaced by other cooling packs such as cooling gel packs or endothermic chemical packs when these cooling packs are available.

Figure 23:
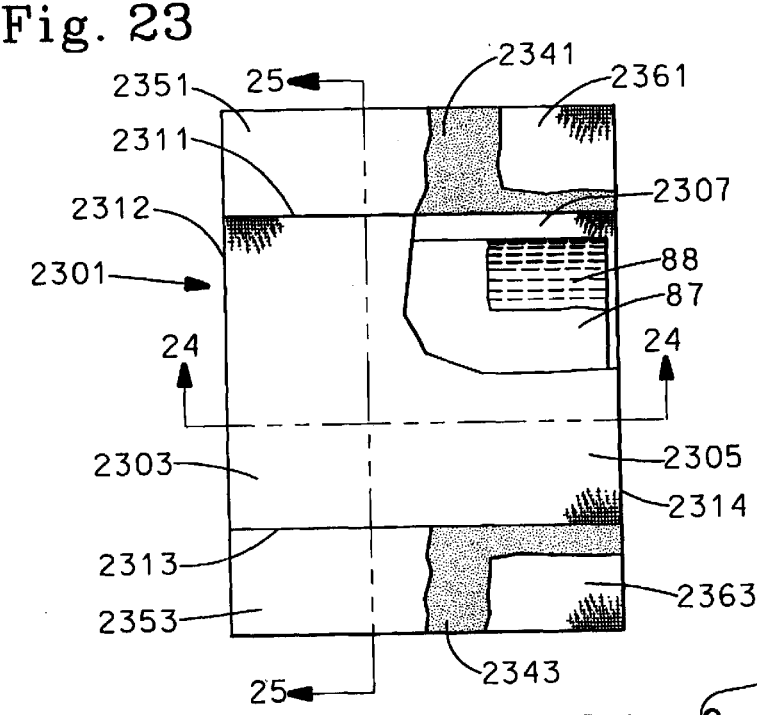
FIG. 23 is a plan view of an alternative embodiment of the self-adhering ice bag device of the present invention, comprising an outer cover with a sack structure which is closed at all four edges, contains an inner cooling gel pack, and has two extended peripheries covered with mounting adhesive.
Figure 25:
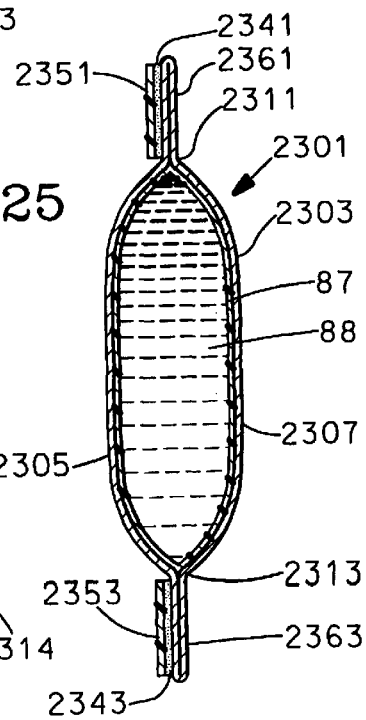
FIG. 25 is a cross-sectional view of the ice bag device of FIG. 23 taken along the line 25—25.
Figure 24:
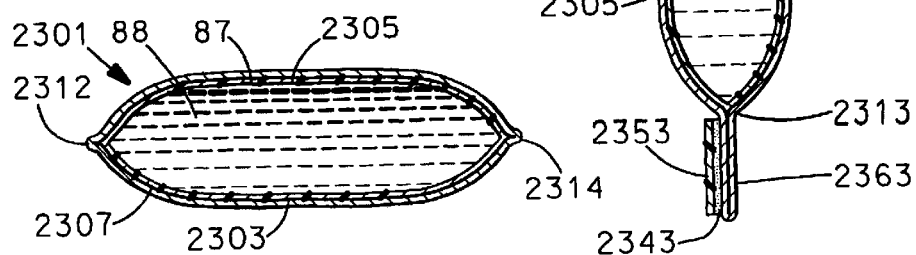
FIG. 24 is a cross-sectional view of the ice bag device of FIG. 23 taken along the line 24—24.
Figure 26:
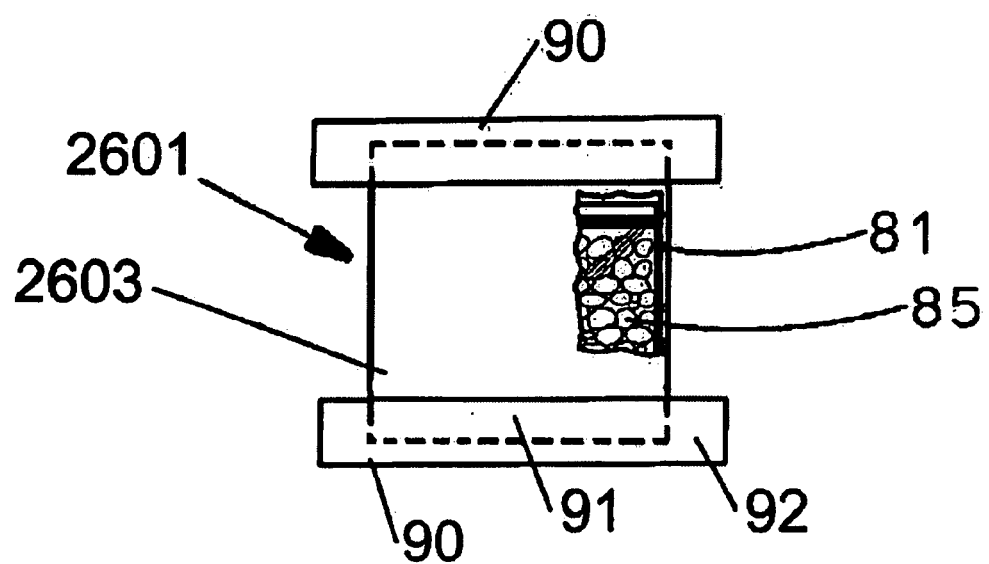
FIG. 26 is a plan view of a self-adhering ice bag device of the present invention, showing the ice bag device secured to the garment with adhesive tapes.

FIGS. 23, 24, and 25 are three different views of an alternative embodiment of the self-adhering ice bag device of the invention, designated as 2301, comprising a closed outer cover 2303 that contains a sealed inner cooling pack 87 containing a cooling gel 88. FIG. 23 is a plan view of the ice bag device 2301. FIG. 24 is a cross-sectional view of the ice bag device 2301 taken along the line 24—24. FIG. 25 is a cross-sectional view of the ice bag device 2301 taken along the line 25—25. The outer cover 2303 has a sack structure having face 2305 and face 2307, four closed edges 2311, 2312, 2313, and 2314, and two extended peripheries 2361 and 2363 that are extensions from edges 2311 and 2313, respectively. The extended peripheries 2361 and 2363 are covered with mounting adhesive layers 2341 and 2343 that are on the same side as face 2305. In turn, the adhesive layers 2341 and 2343 are covered with the release paper strips 2351 and 2353. For ready use, the ice bag device 2301 is stored in a conventional household freezer to cool the gel 88, then the release paper strips 2351 and 2353 are removed to expose the adhesive strips 2341 and 2343 to affix the ice bag device 2301 containing the cooling gel pack 87 to the surface of a garment at a location which is in close contact with the injured area of the user. The cooling gel pack 81 can optionally be replaced by other cooling packs such as a frozen ice pack or an endothermic chemical pack. FIG. 23 also shows the outer cover 2303 partly cut away to show the sealed inner cooling pack 87 (which is also partially broken away to show the cooling gel 88), and part of face 2307. In FIG. 23 a portion of the release paper strips 2351 and 2353 and a portion of the adhesive strips 2341 and 2343 are broken away to show part of the underlying extended peripheries 2361 and 2363, and part of the adhesive strips 2341 and 2343.

In general, it is important to promptly treat any trauma that damages the body so as to minimize the damage. Injuries like bruises, strains, etc., can be treated by the application of cold to minimize the damage. It is therefore useful to provide a means of treating such injuries promptly with cold.

In order to provide such means, one can either provide: (1) a non-constrictive ice bag device comprising a flexible outer cover for a cooling medium, having a layer of mounting adhesive to temporarily attach said cover, when it is filled with the cooling medium (when the cover is liquid impermeable) or one or more inner "cooling bags", or inner cooling packs, hereinafter simply "pack" or "packs", containing the cooling medium, to the inside or the outside of a garment, such that said cooling medium is in close contact with an injured body part of a user, without the need for a strapping and/or wrapping means, wherein the flexible outer cover is preferably a unitary structure, typically either a sack structure (or pouch structure) with one open end to receive one or more inner cooling packs, wherein each cooling pack comprises either a resealable or a sealed fluid impermeable, preferably plastic, container containing a cooling medium, or a closed sack structure containing one or more inner cooling packs, wherein each cooling pack comprises a permanently sealed fluid impermeable plastic container containing a cooling medium (In a preferred embodiment, the outer cover is self-adhering with the adhesive layer being an integral part of the outer cover and entirely or partially covering one side of the outer cover. In another preferred embodiment, the outer cover is not self-adhering, but with the adhesive layer being separated from the outer cover and being in the form of one or more adhesive strips, such as bandage adhesive strips or adhesive bandage strips, that are used to attach the outer cover to the garment. The adhesive layer is optionally, but preferably, covered with a release paper layer to protect the adhesive from prematurely sticking to a surface other than the intended user's garment.); (2) a non-constrictive ice bag device comprising a flexible ice bag outer cover which is filled with a cooling medium (when the cover is liquid impermeable) or at least one inner "cooling bag", or inner cooling pack, containing cooling medium, preferably said outer cover having an extended periphery on at least one side to permit attaching said outer cover, when it is assembled and filled with the cooling medium or at least one cooling pack containing cooling medium, to the inside or the outside of a garment using a plurality of safety pins, wherein "plurality" is typically from 1 to about 20 safety pins, such that said cooling medium is in close contact with an injured body part of an individual, without the need for a strapping and/or wrapping means, wherein said outer cover typically comprises a piece of flexible substrate, such as a piece of fabric, more preferably said outer cover being a sack structure (or pouch structure) with one or more open ends (or sides) and having two or more extended peripheries (or extended sides, or extended edges) that have a width of at least about 0.5 centimeter, more preferably of at least about 1 centimeter, and wherein said cooling medium is contained in either a resealable or sealed, typically flexible, typically plastic, liquid impermeable inner container to form an inner cooling pack, wherein said cooling medium is preferably either ice, ice and water combination, refrigeratable cooling gel, or endothermic chemical cooling system, wherein said inner cooling pack can be inserted through said open end(s) and/or side(s) of said outer cover, and wherein said open end(s) and/or side(s) are capable of being sealed to retain the said inner cooling pack using the said safety pins or the outer cover is sealable or sealed and comprises a liquid impermeable layer and the cooling media is inside the outer cover; and/or (3) an ice bag device comprising a flexible outer cover preferably being a unitary structure, typically either a sack structure (or pouch structure) with one open end or side, or a generally tubular structure with two open ends, with said open ends or sides optionally capable of being sealed, and having dimensions suitable to contain a cooling medium (when the cover is liquid impermeable), or one or more inner cooling packs or bags, wherein each said cooling pack can comprise a generally liquid impermeable container containing cooling media that can be inserted into said outer cover through said open end, and wherein said outer cover has a plurality of small apertures, wherein "plurality" is typically from 1 to about 40, preferably from about 2 to about 20, and more preferably from about 4 to about 10 small apertures, to permit the insertion of one, or more separate, string-like, members that can be used to attach the ice bag device, when it is assembled and filled with at least one cooling pack, to an injured body part of the user; and optionally, but preferably, to permit lacing one of the string-like members through the small apertures in both sides of the bag near each open end of the outer cover to close said open end.

The above covers are normally used to contain one or more inner cooling bags or packs containing a cooling medium. Each inner cooling pack comprises either a resealable or permanently sealed fluid impermeable plastic container containing a cooling medium, preferably either ice, water, ice and water combination, refrigeratable cooling gel, or endothermic chemical cooling mixture. However, if the outer cover is closed, it can contain one or more inner cooling packs, wherein each cooling pack comprises a permanently sealed fluid impermeable plastic container containing a cooling medium, preferably either refrigeratable cooling gel or endothermic chemical cooling mixture.

The above ice bag devices and covers can be used in methods in which first aid treatment of injuries is achieved by attaching the outer covers hereinabove holding one or more inner fluid impermeable plastic containers containing a cooling medium to an injured part, preferably by attachment to a garment so as to apply said cooling medium to an injured body part when the garment is worn. The covers are used in creating a non-constrictive ice bag device, preferably by providing said outer covers, filling one or more plastic zipper containers sealable by interlocking rib and groove sealing closure, with ice or an ice and water combination, placing the filled container(s) inside said outer covers, using an adhesive layer, safety pins, and/or string-like members to attach the assembled ice bag device to the injured part, preferably by attaching the cover inside or outside of a garment, such that said ice bag device is in close contact with an injured body part of the user. The inner cooling pack can comprise a resealable zipper container containing ice and/or an endothermic chemical system pack or a permanently sealed cooling pack containing ice or cooling gel, when such cooling pack is available.

It is important for first aid purposes to associate the covers, etc., with instructions for use to ensure that the method can be practiced efficiently, quickly, and effectively so as to maximize the effect of the cooling treatment on an injury. Preferably, the various parts are combined in an article of manufacture comprising the outer cover(s), optionally, one or more resealable or permanently sealed liquid impermeable containers for the cooling media, optionally, a sealed plastic wrapper to keep the outer cover and the optional elements in a hygienic, non-contaminated condition in storage, and preferably instructions for use. The article can also comprise adhesive strips and/or safety pins, and/or string-like members for purposes of attaching the cover(s) to a garment or a body part.

An adhesive layer or safety pins can be used to attach an ice bag device to a garment such that said ice bag device is in close contact with an injured body part of an individual when the garment is worn, and/or to close the opening of the outer cover of said ice bag device, but it is important to have a periphery which can be penetrated by the pins without puncturing the bag containing the cooling media. Similarly, if string-like members are to be used for attachment of the ice bag device, it is important to provide some small aperture(s) through which the string-like member can be threaded before tying the string-like member around the body part or forming a loop for attachment. Combinations of these attachment means can be used.

The cover(s) and the ice bag(s) are preferably compact, not bulky, preferably washable, and are optionally disposable.

The above description discloses, by way of example, some preferred embodiments of the present invention. However, persons of ordinary skill in the art are capable of creating numerous modifications within the scope of the claims. Changes in specifics of form and details can be made to the above-described embodiments. The claims and not the examples are the measure of the protected invention.

What is claimed is:

1. A flexible outer cover for an ice bag device being a sack structure with one open end, having one face covered with a mounting adhesive layer that can be used to temporarily attach said outer cover to the inside or the outside of a garment, at a location on the garment that is in close contact with the injured area of the body, when the garment is worn, wherein said cover has dimensions to form one or more compartments suitable for containing one or more cooling packs, wherein each cooling pack comprises one inner, generally liquid impermeable, container containing a cooling medium, or for containing a cooling medium when the cover is relatively liquid impermeable, and wherein the adhesive layer is covered with a release layer or is applied immediately before use.

2. A flexible outer cover for an ice bag device that is suitable for use to treat an injured area of a body, said cover being a sack structure with one open end, having one face covered with a mounting adhesive layer that can be used to temporarily attach said outer cover to the inside or the outside of a garment, at a location on the garment that is in close contact with the injured area of the body, when the garment is worn, wherein said cover has dimensions to form one or more compartments suitable for containing one or more cooling packs, wherein each cooling pack comprises one inner, generally liquid impermeable, container containing a cooling medium, or for containing a cooling medium when the cover is relatively liquid impermeable, and wherein the adhesive layer is covered with a release layer or is applied immediately before use, wherein said cover either has a generally rectangular or square configuration when flattened; or wherein said adhesive layer can either cover one entire face of the outer cover or cover only part of that face as one or more adhesive strips; or wherein said cover has a generally rectangular or square configuration when flattened and said adhesive layer can either cover one entire face of the outer cover only part of that face as one or more adhesive strips.

3. The outer cover of claim 2 wherein said adhesive strips cover one or more edges of the outer cover; or wherein each adhesive strip has a width of at least about 1 cm.; or wherein said adhesive strips cover one or more edges of the outer cover and each adhesive strip has a width of at least about 1 cm.

4. The outer cover of claim 2 wherein said outer cover optionally has a mounting adhesive layer on its face, and has from 1 to 4 extended peripheries from the edges of said outer cover, wherein each extended periphery is optionally covered with a mounting adhesive layer that can be used to temporarily attach said outer cover to a garment, in addition to or instead of the adhesive layer on the face of the outer cover, and wherein said adhesive layer is covered with a release layer.

5. The outer cover of claim 1 wherein said outer cover has a periphery extended from the edge of the open end, wherein said periphery has an adhesive layer covering the reverse side of the periphery with respect to the mounting adhesive layer side, for use as a closing means to retain the cooling pack(s) in the outer cover.

6. The outer cover of claim 1 wherein said adhesive layer is renewed after use by either using double-sided adhesive strips that are applied over the original adhesive layer or by removing the adhesive strips and replacing them with new strips.

7. The outer cover of claim 1 wherein said cover is made of material which is either woven, knitted, crocheted, non-woven fabric of natural and/or synthetic fibers, felt, velvet, flocked material, heat-bonded plastic fiber material, solvent-laid thermally bonded plastic fiber material, open-cell plastic foam, close-cell plastic foam, porous plastic film, nonporous plastic film, rubber, paper, and/or laminated materials.

8. An ice bag device comprising:
   (a) a flexible outer cover according to claim 1; and
   (b) at least one cooling pack which optionally comprises a resealable, fluid impermeable plastic container containing ice or ice and water mixture, said resealable fluid impermeable plastic container optionally comprising a rib and groove sealing closure, and said resealable fluid impermeable plastic container optionally being a commercially available zipper bag.

9. An ice bag device comprising:
   (a) a flexible outer cover according to claim 1; and
   (b) at least one cooling pack which comprises a permanently sealed fluid impermeable plastic container containing a cooling medium which is selected from the group consisting of water, cooling gel, or endothermic chemical cooling system.

10. An ice bag device for use to be attached to the inside or the outside of a garment, at a location on the garment that is in close contact with the injured area of the body, when the garment is worn, comprising: a flexible outer cover according to claim 1 wherein said outer cover has a closed sack structure, and at least one cooling pack wherein each cooling pack comprises one inner, generally liquid impermeable, sealed container containing a cooling medium.

11. An ice bag device comprising:
   (a) a flexible outer cover according to claim 1; and
   (b) at least one plastic liquid impermeable inner container suitable for holding a cooling medium to form a cooling pack, wherein said inner container either is completely sealed and contains a cooling gel or water, or an endothermic chemical cooling system, or has one open side that can be closed by means of a resealable closure and contains ice or an ice and water mixture, and wherein said cooling packs have dimensions that enable them to fit inside the outer cover, said inner container optionally being a commercially available zipper bag containing ice or an ice and water mixture.

12. A method for first aid treatment of injuries by using a flexible outer cover for an ice bag device that is suitable for use to treat an injured area of a body, said cover being a sack structure with one open end, having one face covered with a mounting adhesive layer that can be used to temporarily attach said outer cover to the inside or the outside of garment, at a location on the garment that is in close contact with the injured area of the body, when the garment is worn, wherein said cover has dimensions to form one or more compartments suitable for containing one or more cooling packs, wherein each cooling pack comprises one inner, generally liquid impermeable, container containing a cooling medium, or for containing a cooling medium when the cover is relatively liquid impermeable, and wherein the adhesive layer is covered with a release layer or is applied immediately before use, said cover comprising a mounting adhesive layer to temporarily attach the said outer cover holding an inner container containing a cooling medium, to a garment to apply said cooling medium to an injured body part when the garment is worn.

13. A method for treating an injured body part comprising creating an ice bag device for attaching to the inside or the outside of a garment, such that said ice bag device is in close contact with said injured body part when the garment is worn, by using first aid adhesive tape and/or sport tape to attach said ice bag device to said garment, wherein said ice bag device comprises an inner plastic zipper container containing ice or an ice and water combination, said zipper container optionally being a commercially available zipper bag.

14. A method for creating an ice bag device for attaching to the inside or the outside of a garment, such that said ice bag device is in close contact with an injured body part of the user when the garment is worn, by using a double-sided adhesive tape to attach said ice bag device to said garment, wherein said ice bag device comprises (a) an inner plastic zipper container, optionally a commercially available zipper bag, containing ice or an ice and water combination; or (b) an outer cover containing an inner plastic zipper container of claim 12 containing ice or an ice and water combination.

15. An article of manufacture comprising the following elements: one or more flexible outer covers according to claim 1, optionally one or more empty zipper bag containers, or one or more sealed fluid impermeable containers containing water, refrigeratable cooling gel, or endothermic chemical cooling system, optionally a seal plastic film wrapper to contain one or more of said elements, and optionally, packaged in association with a set of instructions that tells a user how to use the cover to assemble an ice bag device, and/or how to use the product properly, and/or to ensure that the user knows what benefits can be achieved, and/or how best to obtain these benefits, wherein the instructions are in one or more languages, and wherein the instructions are in words or words in combination with illustrative images and/or icons, said article optionally comprising one said outer cover and the corresponding number of empty plastic zipper containers to form cooling packs to be placed in the compartment(s) of the said outer cover, wherein said cover has one or more compartments to contain said cooling packs, and said outer cover optionally having dimensions suitable to contain one inner cooling pack.

16. The article of claim 15 comprising one or more flexible outer covers and one refrigeratable gel pack.

17. The article of claim 15 wherein said set of instructions comprises one or more of the following instructions:
(a) place the outer cover on a location either inside or outside of a garment such that said cover is in close contact with the injured area of the body when the garment is worn;
(b) attach the outer cover to the garment using the mounting adhesive layer;
(c) attach the outer cover to the inside of the garment if there is room inside the garment to fit the complete ice bag device and/or if the garment is composed of one or more thick layers of fabrics, or attach the outer cover to the outside of the garment if the garment is made of thin material that allows good transmission of cold to the injured body part and/or if there is not enough room inside the garment;
(d) fill one or more plastic zipper bags with ice for use as the inner cooling packs;
(e) pre-cool one or more gel packs for use as the inner cooling packs;
(f) activate one or more chemical cool pack for use as the inner cooling packs;
(g) place the filled inner cooling pack(s) in the compartment(s) of the outer cover;
(h) close the open end of the outer cover with the extended periphery covered with adhesive, when said extended periphery is available;
(i) wear the garment to apply the attached ice bag device over the injured part; and/or
(j) optionally, apply the ice bag device directly on the skin surrounding the injury using the mounting adhesive, wherein the ice bag device comprises an outer cover having a sack structure with one open end, two or more extended peripheries with only said extended peripheries being covered with mounting adhesive, said set of instructions optionally further comprising one or more of the following instructions: (k) the instruction to direct the consumer to keep one or more said articles in their first-aid kit; (l) the instruction to direct the consumer to a source of ice, including a home refrigerator, ice boxes or ice coolers for beverages at a sport game, and/or a fast food restaurant and/or a hotel or motel on a trip; and/or (m) the instruction disclosing the non-constrictive nature and/or benefit.

18. The article of claim 15 wherein said set of instructions is printed on one or more of: the package, the wrapper, and/or an accompanying instruction flyer or booklet; and/or is communicated via print and/or electronic mass media, optionally selected from newspapers, magazines, radio, television, internet, circulars to members of sport and/or outdoor organizations, and combinations thereof.

19. The article of claim 15 wherein said article carries indicia on one or more of: the outer cover, the inner containers, the wrapper, the package, and/or the set of instructions, showing one or more of: a logo, emblem, symbol, motif, sign, figure, mark, icon, pictogram, insignia, design, image, description, and/or advertisement for one or more of: a sport league, sport franchise, sport sponsor, non-profit or governmental organization, and/or for-profit commercial or industrial organization.

20. The method of doing business wherein the article of claim 15 is distributed with the approval of one or more entities having an association with individuals that are likely to be injured and need an ice bag device on an urgent basis, said entity optionally being an amateur or professional athletic association and/or optionally, attaching the indicia of at least one of said entities to said article and/or associating said indicia with said article.

* * * * *